United States Patent
Kumar

(10) Patent No.: US 9,267,128 B2
(45) Date of Patent: Feb. 23, 2016

(54) PROTEASES FOR DEGRADING GLUTEN

(75) Inventor: Pawan Kumar, Belmont, CA (US)

(73) Assignee: Alvine Pharmaceuticals, Inc., San Carlos, CA (US)

( * ) Notice: Subject to any disclaimer, the term of this patent is extended or adjusted under 35 U.S.C. 154(b) by 0 days.

(21) Appl. No.: 14/008,478

(22) PCT Filed: Mar. 30, 2012

(86) PCT No.: PCT/US2012/031502
§ 371 (c)(1),
(2), (4) Date: Dec. 6, 2013

(87) PCT Pub. No.: WO2012/135646
PCT Pub. Date: Oct. 4, 2012

(65) Prior Publication Data
US 2014/0328818 A1   Nov. 6, 2014

Related U.S. Application Data

(60) Provisional application No. 61/469,507, filed on Mar. 30, 2011.

(51) Int. Cl.
| | |
|---|---|
| *A61K 38/54* | (2006.01) |
| *A61K 38/43* | (2006.01) |
| *C12N 9/64* | (2006.01) |
| *A61K 38/48* | (2006.01) |
| *A23L 1/03* | (2006.01) |

(52) U.S. Cl.
CPC ............... *C12N 9/6405* (2013.01); *A23L 1/034* (2013.01); *A61K 38/48* (2013.01); *A61K 38/4806* (2013.01); *A61K 38/4813* (2013.01); *A61K 38/4873* (2013.01); *A23V 2002/00* (2013.01)

(58) Field of Classification Search
CPC ............................... A61K 38/54; A61K 38/43
See application file for complete search history.

(56) References Cited

U.S. PATENT DOCUMENTS

| | | | |
|---|---|---|---|
| 7,303,871 | B2 | 12/2007 | Hausch et al. |
| 7,320,788 | B2 | 1/2008 | Shan et al. |
| 2003/0215468 | A1 | 11/2003 | Williams et al. |
| 2005/0249719 | A1 | 11/2005 | Shan et al. |
| 2009/0280555 | A1 | 11/2009 | Hausch et al. |
| 2010/0322912 | A1* | 12/2010 | Khosla et al. ............... 424/94.2 |
| 2013/0045195 | A1 | 2/2013 | Kumar |

FOREIGN PATENT DOCUMENTS

| | | | |
|---|---|---|---|
| WO | 2007088062 | A2 | 8/2007 |
| WO | 2008115411 | A1 | 9/2008 |
| WO | 2008115428 | A2 | 9/2008 |
| WO | 2009075816 | A1 | 6/2009 |
| WO | 2010047733 | A2 | 4/2010 |
| WO | 2011028944 | A1 | 3/2011 |

OTHER PUBLICATIONS

Every et al. (Bug damage in New Zealand wheat grain: the role of various heteropterous insets. New Zealand Journal of Crop and Horticultural Science (1992) 20: 3015-312).*

Ayadi et al., "Influence of Tribolium Confusum Development on Selected Physical Properties of Semolina", Journal of Texture Studies (2009), 40(2):225-239.
Bianco-Labra et al., "Purification and characterization of a digestive cathepsin D proteinase isolated from Tribolium castaneum larvae (Herbst)", Insect Biochem MolEC Biol (1996), 26(1):95-100.
Ciccocioppo et al, "The immune recognition of gluten in coeliac disease", Clin Exp Immunol, (2005), 140(3): 408-416.
Coudron et al., "Molecular profiling of proteolytic and lectin transcripts in Homalodisca vitripennis (Hemiptera: Auchenorrhyncha: Cicadellidae) feeding on sunflower and cowpea", Arch Insect Biochem Physiol (2007), 66(2):76-88.
Elpidina et al. "Digestive Peptidase in Tenebrio Molitor and possibility of use to treat celiac disease", Entomological Research (2007), 37(3): 139-147.
Gayle et al., "Identification of regions in interleukin-1 alpha important for activity", J Biol Chem (1993), 268 (29):22105-22111.
Genta et al., "Potential role for gut microbiota in cell wall digestion and glucoside detoxification in Tenebrio molitor larvae", J Insect Physiol (2006), 52(6):593-601.
Goptar et al. "Properties of Post-Proline CleavinG Enzymes from Tenebrio Molitor", Bioorg Khim (May 2008), 34 (3):310-316.
Liang et al. "Inhibition of digestive proteinases of stored grain coleoptera by oryzacystatin, a cysteine proteinase inhibitor from rice seed", FEEBS Lett (Jan. 1991), 278(2):139-142.
NCBI Direct Submission XP 971305.1. Jul. 21, 2008. [Retrieved from the Internet Jul. 18, 2011: <URL: http://www.ncbi.nlm.nih.gov/protein/XP 971305.1>].
Oppert et al. "Compensatory proteolytic responses to dietary proteinase inhibitors in the red flour beetle, Tribolium castaneum (Coleoptera: Tenebrionidae)", Comp Biochem Physiol Part C (Jan. 2005), 140(1):53-58.
Oppert et al. "Digestive proteinases of the larger black flour beetle, Cynaeus angustus (Coleoptera: Tenebrionidae)", Bull Entomol Res (2006), 96(2):167-172.
Prabhakar et al."Sequence analysis and molecular characterization of larval midgut cDNA transcripts encoding peptidases from the yellow mealworm, Tenebrio molitor L", Insect Mol Biol (2007), 16(4):455-468.
Richards et al. "The genome of the model beetle and pest Tribolium castaneum", Nature (Apr. 2008), 452 (7190):949-955.
Singh et al., "Suitability of Packing Materials for Storing Wheat Flour", Bulletin of Grain Technology (Jan. 1979), 17(2)119-124.
Venalanien et al., "Evolutionary relationships of the prolyl oligopeptidase family enzymes", Eur J Biochem (2004), 271(13):2705-2715.
Vinokurov et al. "Digestive proteolysis organization in two closely related Tenebrionid beetles: red flour beetle (*Tribolium castaneum*) and confused flour beetle (*Tribolium confusum*)", Arch Insect Biochem Physiol (Apr. 2009), 70 (4):254-279.
Whisstock et al., "Prediction of protein function from protein sequence and structure", Q Rev Biophys (2003), 36 (3):307-340.
Subramanyam et al. Organophosphate Resistance in Adults of Red Flour Beetle (Coleoptera: Tenebrionidae) and Sawtoothed Grain Beetle (Coleoptera: Cucujidae) Infesting Barley Stored on Farms in Minnesota. Journal of Economic Entomology, (1989), v82(4), p. 989-995.

* cited by examiner

*Primary Examiner* — Karen Cochrane Carlson
*Assistant Examiner* — Natalie Moss
(74) *Attorney, Agent, or Firm* — Pamela J. Sherwood; Bozicevic, Field & Francis LLP

(57) ABSTRACT

Gluten-degrading proteases derived from insects, including flour beetles, are isolated, and the purified, and recombinant forms can be used to make gluten-containing food safe for patients suffering from gluten intolerance.

10 Claims, 1 Drawing Sheet

```
XP_970644    ---------------MVSFFDLVQ-----------EQWGAFKVTHKKQYESETEERFRMK  34
ABR88030     MKFFVLALVFIVGAQAVSFFDLVQ-----------EQWGTFKLQHKKQYKSDTEEKFRMK  49
AF320565     ---------------MLIPSFDIDP-----------QEWLAFKAMHGKNYRNQFEEIFRMK  35
AAF19631     -------------MTRVFVLLALVV-------AANALDWESWKGKYGKSYLGRGEEVLRKR  41
P13277       -----------MKVVALFLFGLAL--------AAANPSWEEFKGKFGRKYVDLEEERYRLN  42
BAK02675     ---------MHAISVLAVLALAFSCTLAFDAKLNQHWKLWKEANNKRYSD-AEEHVRRA    49
XP_970838    ----------------MSPVHAK--------------WAEFKLTHKKQYSSPIEELRRKA  30
ABC88768     -------------MLPKSPFQEQ--------------WSQFKLTHKKSYSSPIEEIRRQL  33
XP_970773    ------------MASPQKLINDQN-------------WSQFKLTHKKEYSTKTEEMKRLA  35
                            .              *  :*    : *      **   *

XP_970644    IFMENAHKVAKHNKLYAQGLVSFKLGVNKYSDMLNHEFVHTLNGYNRSK-TPLR-SGELD  92
ABR88030     IFMENSHKVAKXNKLYEMGLVSYKLKINKYADMLHHEFVHTVNGFNRTKNTPLLGTSEDE 109
AF320565     VFIDNKKKIDEHNAKYELGEASYKMKMNHLGDLMVHEFKALMNGFKKTP--------NAE  87
AAF19631     VWESNLQIVQQHNVLADQGQANYRLGMNTYADLYNEEFMALKGSG-GLL-----QAKDKS  95
P13277       VFLDNLQYIEEFNKKYERGEVTYNLAINQFSDMTNEKFNAVMKG----------YKKGPR  92
BAK02675     TWEGNLQKVQEHNLQADLGVHTYWLGMNKYADMTVTEFVKVMNGYNATM-----RGQRTQ 104
XP_970838    IFQDNLVKIEEEHNAKFAKGEVTYTKAVNQFADMTADEFMAYVNRGLATK------PKMNE  84
ABC88768     IFKDNVAKIAEHNAKFEKGEVTYSKAMNQFGDMSKEEFLAYVNRGKAQK------PKHPE  87
XP_970773    IFTENLSKIDAHNTKYRNGEVTYFKAMNKFGDLTTDEFLAFVNRNKLTK------REKNE  89
                :   *   :  *      *   .:    :*   .*:    :*

XP_970644    ESITFIPPANVELPKQIDWRKLGAVTPVKDQGQCGSCWSFSTTGSLEGQHFRKSKKLVSL 152
ABR88030     QGATFIAPANVKFPENVDWREHGAVTXVKDQGHCGSCWSFSATGALEGQHFRKTNKLVSL 169
AF320565     RNGKIYVPSNENLPKSVDWRQRGAVTPVKDQGHCGSCWSFSATGSLEGQLFLKTGRLVSL 147
AAF19631     STQTFKPLVGVTLPSSVDWRNQGYVTPVKDQGQCGSCWTFSATGSLEGQHFAKTGNLLSL 155
P13277       PAAVFTSTDAAPESTEVDWRTKGAVTPVKDQGQCGSCWAFSTTGGIEGQHFLKTGRLVSL 152
BAK02675     DRHTFSFNSKIALPDTVDWRDKGYVTDVKDQGQCGSCWAFSTTGALEGQHFKQTGKLVSL 164
XP_970838    KLRIPFVKSGKPAAAEVDWRSK-AVTEVKDQGQCGSCWSFSTTGAVEGQLAISGKGLTSL 143
ABC88768     NLRMPYVFSKKPLAASVDWRSN-AVSEVKDQGQCGSCWSFSTTGAVEGQLALQRGGLTSL 146
XP_970773    K-HTKLNTTKIEYETQVDWRANGLVSDVKNEQDCSSSWSFSALGAVEGQLALKTNQLTSL 148
                          :***    *: **::  .*.*.*:**: *.:***    .   * **

XP_970644    SEQNLIDCSE-KYGNNGCNGGLMDNAFRYIKDNGGIDTEQSYPYKAEDEKCHYKPRNKGA 211
ABR88030     SEQNLVDCST-KFGNDGCNGGLMDNAFKYVKYNHGIDTEASYPYHADDEKCHYNPKTSGA 228
AF320565     SEQNLVDCSK-TYGNSGCEGGLMNQAFQYVRDNKGIDTEASYPYEARENNCRFKEDKVGG 206
AAF19631     SEQQLVDCAG-RYGNYGCNGGLMESAYDYIKGVGGVELESAYPYTARDGRCKFDRSKVVA 214
P13277       SEQQLVDCAGGSYYNQGCNGGWVERAIMYVRDNGGVDTESSYPYEARDNTCRFNSNTIGA 212
BAK02675     SEQNLVDCSG-KQGNMGCNGGLMDQAFEYIKENNGIDTEDSYPYEAVDNQCRFKAANVGA 223
XP_970838    SEQNLVDCSS-QYGNAGCNGGWMDSAFDYIHDN-GIMSESAYPYTAMDGNCRFDASQSVT 201
ABC88768     SEQNLIDCSS-SYGNAGCDGGWMDSAFSYIHDY-GIMSESAYPEAQDDYCRFDSSQSVT  204
XP_970773    SAQNLIDCSA-DFG---CNGGHATNAYSYISQF-GIMPEKDYPYEGKAGVCRFDASKSIT 203
             * *:*:**:    *:**  * *:    *: * ***  .    *:::.

XP_970644    TDRGFVDIESGDEEKLKAAVATVGPISVAIDASHPTFQQYSEGVYYEPECS--SEQLDHG 269
ABR88030     TDRGFVDIPTGDEEKLMAAVATVGPVSVAIDASHESFQLYSEGVYYDPECS--SEELDHG 286
AF320565     TDKGYVDILEASEKDLQSAVATVGPISVRIDASHESFQFYSEGVYKEQYCS--PSQLDHG 264
AAF19631     TCKGYVVIPVGDEQALMQAVGTIGPVASIDASGYSFQLYESGVYDFRRCS--STNLDHG  272
P13277       TCTGYVGIAQGSESALKTATRDIGPISVAIDASRSFQSYYTGVYYEPSCS--SSQLDHA  270
BAK02675     TDTGFTDITSKDESALQQAVATVGPISVAIDAGHTSFQLYKHGVYNEPFCS--QTRLDHG 281
XP_970838    SLQGYYDIPSGDESALQDAVANNGPVAVALDAT-EELQLYSGGVLYDTTCS--AQALNHG 258
ABC88768     TLSGYYDLPSGDENSLADAVGQAGPVAVAIDAT-DELQFYSGGLFYDQTCN--QSDLNHG 261
XP_970773    TVTGFYDIDPNDETALQGALAMMGPIAATIEAT-EELQFYKGGILLDEKCNSKVPDLNHG 262
              :  *:   :   .*    *    **::.  ::*   :* * *:     *.     *:*.

XP_970644    VLVVGYGTDEDGNDYWLVKNSWGDSWGDQGYIKMARNRDNNCGIATQASYPLV- 322
ABR88030     VLVVGYGTDENGQDYWIVKNSWGESWGEQGYIKMARNRDNNCGIATQASYPLV- 339
AF320565     VLTVGYGT-ENGDYWLVKNSWGPSWGESGYIKIARNHKNHCGIASMASYPVV-  316
AAF19631     VLAVGYGT-EGGQNYWLVKNSWGPGWGDQGYIKMSKDKNNQCGIATDSCYPL-- 323
P13277       VLAVGYGS-EGGQDFWLVKNSWATSWGESGYIKMARNSRGCGIATDACYPT--  321
BAK02675     VLAVGYGT-DSGKDYWLVKNSWGDKGYIKMTRNKRNQCGIATAASYPLV-    333
XP_970838    VLVVGYGS-EGGQDYWIVKNSWGSGWGEQGYWRQARNRNNNCGIATAASYPALV 311
ABC88768     VFVVGYGS-DNGQDYWILKNSWGSGWGENGYWTQVRNYGNNCGIATAASYPALV 314
XP_970773    VLVVGYGS-ENGGDFWIVKNSWGSDWGEGGYYRPVRNHGNNCGIASSATLPILV 315
              *:.****: :.* ::*::****.  .**: **    ::  *:****: :  *
```

PROTEASES FOR DEGRADING GLUTEN

BACKGROUND OF THE INVENTION

1. Field of the Invention

The present invention provides isolated, purified, and recombinant forms of gluten-degrading proteases and methods for their use in degrading gluten in food. The invention therefore relates to the fields of biology, food preparation, medicine, and molecular biology.

2. Description of Related Disclosures

Celiac disease, also known as celiac sprue, and dermatitis herpetiformis ("DH") are autoimmune diseases (and may be different manifestations of the same disease), and gluten sensitivity is a condition (collectively, celiac disease, DH, and gluten sensitivity are referred to herein as "gluten intolerance") triggered by dietary gluten, a storage protein found in wheat and other cereals. Patients concerned with a potential for gluten intolerance may be advised or choose on their own to refrain from consuming gluten in any amount. Because gluten is a common protein in food, however, patients find it very difficult to avoid gluten and frequently experience relapse due to inadvertent disclosure.

U.S. Pat. No. 7,303,871 describes therapies decreasing adverse effects of gluten ingestion, which involve pre-treatment of gluten-containing food with a protease as well as the use of orally administered proteases to degrade gluten contemporaneously with its ingestion. U.S. Pat. No. 7,320,788 describes admixtures of proteases useful in these therapies, including an admixture of a prolyl endopeptidase (PEP), such as *Sphingomonas capsulata* PEP, and a glutamine endoprotease, such as EPB2 from barley. One such admixture formulated for oral administration and composed of recombinant forms of the barley EPB2 and the *S. capsulata* PEP (termed, respectively, ALV001 and ALV002; see PCT Pub. Nos. 2008/1115411 and 2008/115428) is currently in clinical trials. Each of the aforementioned patents and patent publications is specifically incorporated herein by reference.

To be effective upon oral administration, a protease must be active or, if in a zymogen form, activate and remain active long enough to degrade any gluten present into non-immunogenic fragments. The immunogenic peptides can be relatively small (~10 amino acids) and are contained, often in multiple copies, in very large proteins. The conditions in the gastrointestinal tract are harsh, and any exogenously added protease is typically degraded, and so rendered inactive, quickly. Accordingly, there remains a need in the art for proteases useful in the treatment of gluten intolerance. The present invention meets that need.

SUMMARY OF THE INVENTION

In a first aspect, the present invention provides gluten-degrading, glutamine-specific proteases from eukaryotic cells, including but not limited to insect cells, including but not limited to proteases from insects that derive protein from dried grain products. Such insects include, without limitation, flour beetles, e.g. members of the darkling beetle genera *Tribolium* or *Tenebrio*, which are pests of cereal silos. Species of interest for obtaining gluten-degrading proteases useful in the methods and compositions of the invention include *Tribolium castaneum* (red flour beetle), *Tenebrio molitor* (yellow meal worm and other organisms that consume proteins from dried grain products, particularly gluten-containing products, during their development, in isolated, purified, and recombinant form. Proteases of the invention are also provided, in some embodiments, in PEGylated form; see PCT Pub. No. 2007/047303, incorporated herein by reference.

In a second aspect, the present invention provides recombinant expression vectors for the proteases of the invention and methods for using such vectors to produce the encoded proteases.

In a third aspect, the present invention provides methods for degrading gluten in food, comprising contacting gluten-containing food with a protease of the invention in an isolated, purified, or recombinant form. Such methods also include the use of the proteases in combinations, including combinations of two or more insect-derived proteases, for example a combination of a proline specific protease, including but not limited to those described in PCT Pub. No. 2011/126873, incorporated herein by reference, and a glutamine specific protease described herein. In other embodiments, the insect-derived protease may be combined with a non-insect protease, e.g. *Hordeum vulgarum* endopeptidase C, *Sphingomonas capsulata* prolyl endopeptidase (PEP), and the like, including but not limited to any protease described in U.S. Pat. Nos. 7,320,788 and 7,628,985, incorporated herein by reference. A "combination", as used herein, refers to two or more proteases that can be administered in accordance with the invention either contemporaneously in separate formulations, or simultaneously in a unit dose form in which two or more proteases are co-formulated. In many embodiments, the protease or combination of proteases is ingested by an individual contemporaneously with food, e.g. at mealtime, either immediately before, during, and/or after ingestion of a meal or snack.

In a fourth aspect, the present invention provides pharmaceutical formulations and unit dose forms suitable for oral administration and containing a protease or combination of proteases as provided by the invention, in an isolated, purified, or recombinant form admixed with one or more pharmaceutically acceptable excipients. Suitable excipients include those disclosed in PCT Publication Nos. 2007/044906; 2008/115411; 2010/021752; and 2010/042203, each of which is incorporated herein by reference.

In a fifth aspect, the present invention provides a method for treating gluten intolerance in a patient in need of such treatment, wherein said treatment reduces the exposure of said patient to immunogenic gluten peptides, said method comprising the step of orally administering to said patient a therapeutically effective dose of a protease of the invention in an isolated, purified, or recombinant form, or a combination of proteases that comprises at least one protease of the invention, or a pharmaceutical formulation thereof contemporaneously with the ingestion of a food that may contain gluten. In one embodiment, the patient has been diagnosed with celiac disease. In another embodiment, the patient has been diagnosed with dermatitis herpetiformis. In another embodiment, the patient has not been diagnosed as having any form of gluten intolerance or gluten sensitivity but simply prefers not to consume gluten.

In some embodiments of the invention, the gluten-degrading, glutamine-specific protease is a protease derived from *Tribolium castaneum*. In some such embodiments the protease comprises the sequence set forth in SEQ ID NO:1, 2 or 3, particularly SEQ ID NO:2. In some such embodiments the protease sequence is fused to a sequence composed of six histidines (6×his tag) and a thrombin cleavage site. In other embodiments, the protease sequence is free of a six histidines (6×his tag) and thrombin cleavage site. In some embodiments the protease is provided as a pro-enzyme, which can, for example, be activated upon exposure to low pH. In other embodiments the protease is provided as the mature enzyme form. Polynucleotide sequences encoding such a protease are also provided, which sequences are exemplified but not limited to the polynucleotide sequences provided in SEQ ID NO:10, 11 and 12. It will be understood by one of skill in the art that multiple polynucleotide sequences encode any single amino acid sequence.

These and other aspects and embodiments of the invention are described in more detail below.

BRIEF DESCRIPTION OF THE DRAWINGS

FIG. 1. Alignment of glutamine specific protease sequences and determination of consensus sequence. Asterisks indicate strictly conserved positions and colons and periods indicate full conservation of strong and weak groups, respectively below the multiple sequence alignment. Aligned sequences are (SEQ ID NO:1) XP_970644 from *Tribolium castaneum*; (SEQ ID NO:2) XP_970838 from *Tribolium castaneum*; (SEQ ID NO:3) XP_970773 from *Tribolium castaneum*; (SEQ ID NO:4) ABC88768 from *Tenebrio molitor*; (SEQ ID NO:5) ABR88030 from *Dermestes frischii*; (SEQ ID NO:6) AAF19631 from *Myxine glutinosa*; (SEQ ID NO:7) AF320565 from *Rhodnius prolixus*; (SEQ ID NO:8) BAK02675 from *Hordeum vulgare* subsp. *vulgare*; SEQ ID NO:9) P13277 from *Homarus americanus*. Across the alined proteases, the sequence identity is greater than 50% and the sequence similarity (relaxed for similar substitutions) is greater than 64%.

DETAILED DESCRIPTION OF THE EMBODIMENTS

The present invention provides gluten-degrading glutamine-specific proteases derived from eukaryotic cells in isolated, purified, and/or recombinant form. Some of the favorable properties of these proteases with respect to degrading gluten in foodstuffs and/or in the gastrointestinal tract include: resistance to degradation by proteases in the gastrointestinal (GI) tract providing longer duration of activity in the GI tract; broad substrate size tolerance that enables degradation of immunogenic gluten peptides regardless of the size of the peptide or protein in which they may be located; synergy with proteases in gluten-degrading activity; broad pH stability and activity range that facilitates optimal activity under acidic gastric conditions; favorable kinetics enabling degradation of gluten before gastric emptying occurs; resistance to oxidizing conditions that may be encountered in certain food stuffs and low $K_m$ for gluten, enabling gluten degradation even at low gluten concentrations. The broad pH stability of the proteases of the invention provide for stability at high pH, e.g. as may be encountered in contact with foodstuffs, and stability at low pH, e.g. as may be encountered in the digestive system.

In some embodiments of the invention, a glutenase of the invention is derived from a flour beetle, e.g. members of the darkling beetle genera *Tribolium* or *Tenebrio*, which are pests of cereal silos. Flour beetles of interest include, without limitation, *Tribolium castaneum* (red flour beetle); *Tribolium confusum* (confused flour beetle); *Tribolium destructor* (destructive flour beetle); *Tenebrio molitor* (mealworm beetle); *Tenebrio obscurus*; etc. Reference may be made to descriptions of flour beetle proteases, e.g. Vinokurov et al. (2009) Arch Insect Biochem Physiol. 70(4):254-79; Goptar et al. (2008) Bioorg Khim. 34(3):310-6; Oppert et al. (2006) Bull Entomol Res. 96(2):167-72; Oppert et al. (2005) Comp Biochem Physiol C Toxicol Pharmacol.; and Liang et al. (1991) FEBS Lett. 278(2):139-42, each specifically incorporated herein by reference.

The amino acid sequences of exemplary proteases of the invention are listed by reference to SEQ ID NO and other identifying information in Table 1, below, and in the sequence listing as proteins (SEQ ID NO:1-4) and encoding nucleotide sequences (SEQ ID NO:10-13). The sequence listing for the insect-derived glutamine proteases provide the protease amino acid sequence. The provided amino acid sequence can be optionally modified to additionally comprise a sequence composed of six histidines (6×his tag) and a thrombin cleavage site (LVPRGS), e.g. at the C-terminus. The coding sequences set forth in SEQ ID NO:10-13 exemplify this embodiment. This optional additional sequence facilitates purification using metal affinity chromatography of the recombinant protease that contains it, as the 6×his tag binds to appropriate chromatography resin and the thrombin cleavage site facilitates removal of the 6×his tag, if that is desired, prior to formulation of the protease. For large scale commercial purification the 6-his tag can be omitted, as the present invention provides for a protease sequence in absence or presence of a 6his tag and cleavage site. The nucleotide sequences may be modified from the native sequence to be optimized for expression both in *Pichia pastoris* and *Escherichia coli* (SEQ ID NO:10-13). Regions of the sequences contain restriction sites introduced by recombinant DNA technology (XhoI on 5' and KpnI on 3' end) to facilitate cloning into an *E. coli* expression vector (pET28b) in SEQ ID NO 10-13.

With respect to the noted Genbank reference amino acid sequences, SEQ ID NO:1 has been modified to replace the signal sequence, residues 1-16, with a methionine. SEQ ID NO:2 has been modified to replace the signal sequence, residues 1-19, with a methionine. SEQ ID NO:3 has not been modified. SEQ ID NO:4 has been modified to replace the signal sequence, residues 1-16, with a methionine.

TABLE 1

Examples of glutamine specific proteases from insects.

| SEQ ID NO: | Pubmed Protein ID/Gene ID | Similarity to |
| --- | --- | --- |
| 1, 10 | XP_970644/LOC659226 | Cathepsin-L, EP-B2 |
| 2, 11 | XP_970838*/LOC659441 | Cathepsin-L, EP-B2 |
| 3, 12 | XP_970773/LOC659367 | Cathepsin-L, EP-B2 |
| 4, 13 | ABC88768/DQ_356053 | Cathepsin-L, EP-B2 |

*currently replaced with accession number NP_001163996

As used herein, the term "glutamine specific protease" refers to the ability of a protease to cleave a peptide or protein substrate at the amide bond following a glutamine residue and is not intended to imply that the protease is unable to cleave other amide bonds.

In some embodiments, a protease of the invention is subject to cleavage or removal of sequences that are not required for activity, as well as the removal of sequences that have to be removed before the protease is active, for example zymogen activation. Zymogens are inactive forms of proteases that are converted to the active protease by proteolytic cleavage of a propeptide. In some embodiments the proteaseis of the invention is used as a zymogen, where the propeptide form is delivered and activated at the site of action (i.e., in the saliva or stomach) or preactivated prior to or contemporaneously before contacting them with a gluten-containing food. In other embodiments the mature form of the enzyme is used. For example, a zymogen form of a protease may be used to facilitate production or processing, and then, prior to use, be subjected to treatment such that the pro-peptide region of the zymogen is cleaved (and optionally purified away from the active protease). Such pre-activation of a zymogen form may be employed, e.g., to simplify the dosing formulation and/or to reduce the need for activation at the site of action.

The proteases of the invention include propeptides. For example, in SEQ ID NO:1, residues 12-71 may constitute the propeptide region, with a protease region at residues 106-320. In SEQ ID NO:2, residues 8-67 may constitute the propeptide region, with a protease region at residues 99-308. In SEQ ID NO:3, residues 13-72 may constitute the propeptide region, with a protease domain at residues 103-312. In SEQ ID NO:4, residues 11-70 may constitute the propeptide region, with a protease domain at residues 102-311. It will be understood by one of skill in the art that alternative or multiple cleavage sites may be present in a proenzyme and can alternatively used, so long as the processed peptide has the desired mature enzyme activity.

Included as a glutamine-specific protease is a protease shown in Table 1 or a protease derived from a eukaryotic cell that has homology to a protease shown in Table 1, or a variant of either. In one embodiment, the protease is an insect-derived protease, e.g. a flour beetle protease. Thus, the invention provides, in addition to the specific insect sequences set forth in Table 1 (SEQ ID NO:1-4 and 10-13), variants, homologs and orthologs of the provided sequences.

A variant can be substantially similar to a native sequence, i.e. differing by at least one amino acid, and can differ by at least two but usually not more than about ten amino acids (the number of differences depending on the size of the native sequence). The sequence changes may be substitutions, insertions or deletions. Scanning mutations that systematically introduce alanine, or other residues, may be used to determine key amino acids to be maintained in variant sequences. Homologs or orthologs of the provided sequences include the counterpart proteases in any one of the flour beetles, and will usually have at least about 50% sequence identity at the amino acid level, at least about 75% sequence identity, at least about 80% sequence identity, at least about 85% sequence identity, at least about 90% sequence identity, at least about 95% sequence identity, at least about 99% sequence identity, or more. In various embodiments, a protease of the invention is any protease other than the barley-derived sequence set forth in FIG. 1, defined by a consensus sequence based on multiple alignments of several homologs from various organisms, as provided in FIG. 1. The multiple sequence alignment shown in FIG. 1 was generated using ClustalW2, a general purpose multiple sequence alignment program, where the consensus residues are marked at the bottom of the alignment. As demonstrated by FIG. 1, eukaryotic proteases other than insect proteases share significant homology with the insect proteases of the invention, see, e.g. SEQ ID NO:5-9. Thus, in one embodiment of the invention the proteases is a non-insect protease comprising the amino acid sequence set forth in SEQ ID NO:5-7 or 9, or a protease homologous to the insect proteases set forth in SEQ ID NO:1-4, for example SEQ ID NO:5-7 or 9, or a protease having a degree of homology to any one of SEQ ID NO:1-4 that is commensurate with the degree of homology set forth in FIG. 1.

Conservative amino acid substitutions that can be used to provide a variant sequence of the invention typically include substitutions within the following groups: (glycine, alanine); (valine, isoleucine, leucine); (aspartic acid, glutamic acid); (asparagine, glutamine); (serine, threonine); (lysine, arginine); and (phenylalanine, tyrosine). Homologs or orthologs of the provided sequences include the counterpart proteases in any one of the flour beetles, and will usually have at least about 50% sequence similarity at the amino acid level, at least about 75% sequence similarity, at least about 80% sequence similarity, at least about 85% sequence similarity, at least about 90% sequence similarity, at least about 95% sequence similarity, at least about 99% sequence similarity, or more.

The amino acid sequence of a naturally occurring protease can be altered in various ways known in the art to generate targeted changes in sequence and so provide variant sequences of the invention. Such variants will typically be functionally-preserved variants, which differ, usually in sequence, from the corresponding native or parent protein but still retain the desired or exhibit enhanced biological activity and/or function. Various methods known in the art can be used to generate targeted changes, e.g. phage display in combination with random and targeted mutations, introduction of scanning mutations, and the like, and provide a variant sequence of the invention. Included is the addition of His or epitope tags to aid in purification, as exemplified herein. Enzymes modified to provide for a specific characteristic of interest may be further modified, for e.g. by mutagenesis, exon shuffling, etc., as known in the art, followed by screening or selection, so as to optimize or restore the activity of the enzyme, e.g. to wild-type levels, and so provide other variant sequences of the invention.

The term "protease" also includes biologically active fragments. Fragments of interest include fragments of at least about 20 contiguous amino acids, more usually at least about 50 contiguous amino acids, and may comprise 100 or more amino acids, up to the complete protein, and may extend further to comprise additional sequences. In each case, the key criterion is whether the fragment retains the ability to digest toxic gluten oligopeptides.

Modifications of interest to the protease that do not alter primary sequence but provide other variant proteases of the invention include chemical derivatization of proteins, including, for example, acylation with, e.g. lauryl, stearyl, myristyl, decyl, or other groups; PEGylation, esterification; and/or amidation. Such modifications may be used to increase the resistance of the enzyme toward proteolysis, e.g. by attachment of PEG sidechains or lauryl groups to surface lysines. Also included are modifications of glycosylation, e.g. those made by modifying the glycosylation patterns of a protein during its synthesis and processing or in further processing steps; e.g. by exposing the protein to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

Also useful in the practice of and provided by the present invention are proteins that have been modified using molecular biological techniques and/or chemistry so as to improve their resistance to proteolytic degradation and/or to acidic conditions such as those found in the stomach, and to optimize solubility properties or to render them more suitable as a therapeutic agent.

A protease useful in the practice of the present invention can be identified by its ability to cleave a pretreated substrate to remove toxic ("toxic" as used herein means capable of generating a harmful immune reaction in a celiac disease patient) gluten oligopeptides, where a "pretreated substrate" is a gliadin, hordein, secalin or avenin protein that has been treated with physiological quantities of gastric and pancreatic proteases, including pepsin (1:100 mass ratio), trypsin (1:100), chymotrypsin (1:100), elastase (1:500), and carboxypeptidases A and B (1:100). Pepsin digestion may be performed at pH 2 for 20 min., to mimic gastric digestion, followed by further treatment of the reaction mixture with trypsin, chymotrypsin, elastase and carboxypeptidase at pH 7 for 1 hour, to mimic duodenal digestion by secreted pancreatic enzymes. The pretreated substrate comprises oligopeptides resistant to digestion, e.g. under physiological conditions. A glutenase may catalyze cleavage of pepsin-trypsin-chymotrypsin-elastase-carboxypeptidase (PTCEC) treated gluten such that less than 10% of the products are longer than PQPQLPYPQ (as judged by longer retention times on a C18 reverse phase HPLC column monitored at $A_{215}$). Glutenase assays suitable for characterizing proteases of the invention are also described in U.S. Pat. Nos. 7,303,871; 7,320,788; and 7,534,426, each of which is incorporated herein by reference.

The ability of a protease to cleave a pretreated substrate can be determined by measuring the ability of an enzyme to increase the concentration of free $NH_2$-termini in a reaction mixture containing 1 mg/ml pretreated substrate and 10 µg/ml of the peptidase or protease, incubated at 37° C. for 1 hour. A protease useful in the practice of the present invention will increase the concentration of the free amino termini under such conditions, usually by at least about 25%, more usually by at least about 50%, and preferably by at least about 100%. A protease includes an enzyme capable of reducing the residual molar concentration of oligopeptides greater than about 1000 Da in a 1 mg/ml "pretreated substrate" after a 1 hour incubation with 10 µg/ml of the enzyme by at least about 2-fold, usually by at least about 5-fold, and preferably by at least about 10-fold. The concentration of such oligopeptides can be estimated by methods known in the art, for example size exclusion chromatography and the like.

A protease of the invention includes an enzyme capable of detoxification of whole gluten either alone or in combination with a suitable enzyme, which such suitable enzyme can be either co-formulated or separately formulated and co-administered. While the proteases of the invention can also be used to degrade gluten in foods completely ex vivo, in many embodiments of the invention, the protease of the invention will, even if contacted with the food prior to ingestion, degrade gluten in food in vivo and thus act in concert with proteases in the digestive tract. Gluten detoxificatioin can be monitored using polyclonal T cell lines derived from intestinal biopsies of celiac patients; detoxification of whole gluten as monitored by LC-MS-MS; and/or detoxification of whole gluten as monitored by ELISA assays using monoclonal antibodies capable of recognizing sequences specific to gliadin (see, e.g., U.S. Pat. No. 7,303,871, incorporated herein by reference). A protease of the invention may also include an enzyme that reduces the anti-tTG antibody response to a "gluten challenge diet" in a celiac disease patient by at least about 2-fold, more usually by at least about 5-fold, and preferably by at least about 10-fold. A "gluten challenge diet" is defined as the intake of 100 g bread per day for 3 days by an adult celiac disease patient previously on a gluten-free diet. The anti-tTG antibody response can be measured in peripheral blood using standard clinical diagnostic procedures, as known in the art.

The proteases useful in the practice of the present invention may also be isolated and purified in accordance with conventional methods from recombinant production systems and from natural sources. Protease production can be achieved using established host-vector systems in organisms such as *E. coli, S. cerevisiae, P. pastoris, Lactobacilli, Bacilli* and *Aspergilli*. Integrative or self-replicative vectors may be used for this purpose. In some of these hosts, the protease is expressed as an intracellular protein and subsequently purified, whereas in other hosts the enzyme is secreted into the extracellular medium. Purification of the protein can be performed by a combination of ion exchange chromatography, Ni-affinity chromatography (or some alternative chromatographic procedure), hydrophobic interaction chromatography, and/or other purification techniques. Typically, the compositions used in the practice of the invention will comprise at least 20% by weight of the desired product, more usually at least about 50% by weight, preferably at least about 85% by weight, at least about 90%, and for therapeutic purposes, may be at least about 95% by weight, in relation to contaminants related to the method of preparation of the product and its purification. Usually, the percentages will be based upon total protein. Proteins in such compositions may be present at a concentration of at least about 500 µg/ml; at least about 1 mg/mg; at least about 5 mg/ml; at least about 10 mg/ml, or more. Suitable methods include those described in PCT Pub. No. 2008/115428, incorporated herein by reference.

In one aspect, the present invention provides a purified preparation of an insect-derived protease. Such enzymes may be isolated from natural sources, but the present invention allows them to be produced by recombinant methods. In one embodiment, such methods utilize a bacterial host for expression, although fungal and eukaryotic systems, including insect systems, find use for some purposes. Coding sequences that contain a signal sequence, or that are engineered to contain a signal sequence can be secreted into the periplasmic space of a bacterial host. An osmotic shock protocol can then be used to release the periplasmic proteins into the supernatant.

Where the enzyme is a cytoplasmic enzyme, a signal sequence can be introduced for periplasmic secretion, or the enzyme can be isolated from a cytoplasmic lysate. Methods for purification include Ni-NTA affinity purification, e.g. in combination with introduction of a histidine tag; and chromatography methods known in the art, e.g. cation exchange, anion exchange, gel filtration, HPLC, FPLC, and the like.

For various purposes, such as stable storage, the enzyme may be lyophilized. Lyophilization is preferably performed on an initially concentrated preparation, e.g. of at least about 1 mg/ml. Peg may be added to improve the enzyme stability. It has been found that MX PEP can be lyophilized without loss of specific activity. The lyophilized enzyme and excipients is useful in the production of enteric-coated capsules or tablets, e.g. a single capsule or tablet may contain at least about 1 mg. enzyme, usually at least about 10 mg enzyme, and may contain at least 100 mg enzyme, at least about 500 mg enzyme, or more. Coatings may be applied, where a substantial fraction of the activity is retained, and is stable for at least about 1 month at 4° C.

For purposes of combinations of enzymes, the following non-limiting list of proteases is of interest: *Hordeum vulgare* endoprotease (Genbank accession U19384); X-Pro dipeptidase from *Aspergillus oryzae* (GenBank ID# BD191984); carboxypeptidase from *Aspergillus saitoi* (GenBank ID# D25288); *Flavobacterium meningosepticum* PEP (Genbank ID # D10980); *Sphingomonas capsulata* PEP (Genbank ID# AB010298); *Penicillium citrinum* PEP (Genbank ID# D25535); *Lactobacillus helveticus* PEP (Genbank ID# 321529); and *Myxococcus xanthus* PEP (Genbank ID# AF127082). Combinations of interest may also include two or more insect-derived proteases, for example a combination of a proline specific protease (see, e.g., PCT Pat. Pub. No. 2011/126873, incorporated herein by reference) and a glutamine specific protease described herein. In other embodiments the insect-derived protease may be combined with a non-insect-derived protease, e.g. *Hordeum vulgarum* endopeptidase C, *Sphingomonas capsulata* prolyl endopeptidase (PEP), and the like, including, for example and without limitation, a protease set forth herein may be combined with any protease described in U.S. Pat. Nos. 7,320,788 and 7,628,985. By combination, it is intended that a plurality of proteases are administered contemporaneously in separate formulations, or are co-formulated. In some embodiments the protease or combination of proteases is ingested by an individual contemporaneously with food, e.g. at meal time or at any other time when a food is ingested. The proline- and glutamine-specific proteases described in U.S. Pat. Nos. 7,303,871 and 7,320,788 and in PCT Pub. Nos. 2010/047733, 2009/075816, and 2008/115411, each of which is incorporated herein by reference are especially suitable for use in such combinations The glutamine-specific gluten degrading proteases of the invention provide certain advantages. They are derived from or highly homologous to proteases that naturally reside in the acidic part of the insect digestive system and so their functional pH range is in an acidic range, making them ideal for degrading gluten in the human stomach. The broad pH stability of the proteases of the invention provide for stability at high pH, e.g. as may be encountered in contact with foodstuffs, and stability at low pH, e.g. as may be encountered in the digestive system. The proteases are proteolytically stable to other insect digestive proteases, and because many insect digestive proteases are homologous to human digestive proteases, this property of proteolytic resistance applies to human digestive proteases. The proteases, in their natural environment, have to break down proteins before a meal is excreted and so have favorable kinetics for meal digestion. Many grains use gluten as a storage protein and the proteases of the invention have evolved to breakdown gluten specifically. Gluten is rich in glutamine and proline residues.

The glutamine specific proteases can be combined or otherwise used in combination, in accordance with the present invention, with proline specific proteases, such as the *S. capsulata* prolyl endopeptidase and its recombinant form ALV002 (see PCT Pub. No. 2010/042203), to make highly potent, gluten-degrading mixtures of proteases. In addition, the glutamine-specific proteases of the invention can be combined or otherwise used in combination with other glutamine-specific proteases, including but not limited to barley EPB2 protease and its recombinant form ALV001 (see PCT Pub. No. 2010/042203).

The methods of the invention, as well as tests to determine their efficacy in a particular patient or application, can be carried out in accordance with the teachings herein using procedures standard in the art. Thus, the practice of the present invention may employ conventional techniques of molecular biology (including recombinant techniques), microbiology, cell biology, biochemistry and immunology within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991); as well as updated or revised editions of all of the foregoing.

For the purposes of the present invention, toxic gliadin oligopeptides are peptides derived during normal human digestion of gliadins and related storage proteins from dietary cereals, e.g. wheat, rye, barley, and the like, that are immunogenic in celiac disease patients, e.g., act as antigens for T cells. Immunogenic peptides are usually from about 8 to 20 amino acids in length, more usually from about 10 to 18 amino acids or longer. Such peptides may include PXP motifs. Determination of whether an oligopeptide is immunogenic for a particular patient is readily determined by standard T cell activation and other assays known to those of skill in the art. Determination of whether a candidate enzyme will digest a toxic gluten oligopeptide can be empirically determined. For example, a candidate may be combined with an oligopeptide or with a pretreated substrate comprising one or more of gliadin, hordein, secalin or avenin proteins that have been treated with physiological quantities of gastric and pancreatic proteases. In each instance, it is determined whether the enzyme is capable of cleaving the oligopeptide. The oligopeptide or protein substrates for such assays may be prepared in accordance with conventional techniques, such as synthesis, recombinant techniques, isolation from natural sources, or the like. For example, solid-phase peptide synthesis involves the successive addition of amino acids to create a linear peptide chain (see Merrifield (1963) J. Am. Chem. Soc. 85:2149-2154). Recombinant DNA technology can also be used to produce the peptide.

The level of digestion of the toxic oligopeptide can be compared to a baseline value. Gluten becomes much less toxic when it is degraded to peptides shorter than 10 amino acids in length, such as peptides of 8 amino acids, peptides of 6 amino acids, or shorter peptides. The disappearance of the starting material and/or the presence of digestion products can be monitored by conventional methods in model systems, including in vitro and in vivo assay systems. For example, a detectable marker can be conjugated to a peptide, and the change in molecular weight associated with the marker is then determined, e.g. acid precipitation, molecular weight exclusion, and the like. The baseline value can be a value for a control sample or a statistical value that is representative a control population. Various controls can be conducted to ensure that an observed activity is authentic, including running parallel reactions, positive and negative controls, dose response, and the like.

The present invention also provides recombinant nucleic acids comprising coding sequences for the recombinant proteases of the invention. These recombinant nucleic acids include those with nucleotide sequences comprising one or more codons optimized for expression in *Pichia pastoris, E. coli*, or other host cells heterologous to the cells in which such proteins (or their variants) are naturally produced. Examples of optimized nucleotide sequences are provided in the sequence listing as SEQ ID NO:10-13.

The present invention also provides recombinant expressing vectors comprising nucleic acids encoding the proteases of the invention operably linked to a promoter positioned to drive expression of the coding sequence in a host cell. The present invention also provides methods for producing the proteases of the invention comprising culturing a host cell comprising an expression vector of the invention under conditions suitable for expression of the protease.

As used herein, compounds which are "commercially available" may be obtained from commercial sources including but not limited to Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

Compounds useful for co-administration with the proteases and treated foodstuffs of the invention can also be made by methods known to one of ordinary skill in the art. As used herein, "methods known to one of ordinary skill in the art" may be identified through various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

The proteases of the invention and/or the compounds and combinations of enzymes administered therewith are incorporated into a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the protease and/or other compounds can be achieved in various ways, usually by oral administration. The protease and/or other compounds may be systemic after administration or may be localized by virtue of the formulation, or by the use of an implant that acts to retain the active dose at the site of implantation.

In pharmaceutical dosage forms, the protease and/or other compounds may be administered in the form of their pharmaceutically acceptable salts, or they may also be used alone or in appropriate association, as well as in combination with other pharmaceutically active compounds. The agents may be combined, as previously described, to provide a cocktail of proteolytic activities. The following methods and excipients are exemplary and are not to be construed as limiting the invention.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Gluten detoxification for a gluten sensitive individual can commence as soon as food enters the stomach, because the acidic environment (~pH 2-4) of the stomach favors gluten solubilization. Introduction of a protease into the stomach may synergize with the action of pepsin, leading to accelerated destruction of toxic peptides upon entry of gluten in the small intestines of celiac patients. Such proteases may not require enteric formulation.

In another embodiment, the protease is admixed with food, or used to pre-treat foodstuffs containing glutens. Protease mixed in foods can be enzymatically active prior to or during ingestion, and may be encapsulated or otherwise treated to control the timing of activity. Alternatively, the protease may be encapsulated to achieve a timed release after ingestion, e.g. a predetermined period of time after ingestion and/or a predetermined location in the intestinal tract.

Formulations are typically provided in a unit dosage form, where the term "unit dosage form," refers to physically discrete units suitable as unitary dosages for human subjects, each unit containing a predetermined quantity of protease in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Depending on the patient and condition being treated and on the administration route, the protease may be administered in dosages of 0.01 mg to 500 mg/kg body weight per day, e.g.

about 1-100 mg/kg body weight/per day, e.g., 20 mg/kg body weight/day for an average person. Efficient proteolysis of gluten in vivo for an adult may require at least about 500 units of a therapeutically efficacious enzyme, or at least about 5000 units, or at least about 50,000 units, at least about 500,000 units, or more, for example, about $5 \times 10^6$ units or more, where one unit is defined as the amount of enzyme required to hydrolyze 1 µmol of a chosen substrate per min under specified conditions. It will be understood by those of skill in the art that the dose can be raised, but that additional benefits may not be obtained by exceeding the useful dosage. Those of skill in the art will appreciate that the orally administered proteases of the invention are non-toxic, so the amount of protease administered can exceed the dose sufficient to degrade a substantial amount (e.g., 50% or more, such as 90% or 99%) or all of the gluten in the food with which it is consumed. Dosages will be appropriately adjusted for pediatric formulation. In children the effective dose may be lower. In combination therapy, a comparable dose of the two enzymes may be given; however, the ratio may be influenced by e.g., synergy in activity and/or the relative stability of the two enzymes toward gastric and duodenal inactivation.

Protease treatment of celiac disease or other form of gluten intolerance is expected to be most efficacious when administered before or with meals. However, since food can reside in the stomach for 0.5-2 h, the protease could also be administered up to within 1 hour after a meal. In some embodiments of the invention, formulations comprise a cocktail of selected proteases, for example a combination of a protease of the invention with one or more of *Sphingomonas capsulata* PEP, *Hordeum vulgare* cysteine endoprotease B, and the like. Such combinations may achieve a greater therapeutic efficacy.

Those of skill will readily appreciate that dose levels can vary as a function of the specific enzyme, the severity of the symptoms and the susceptibility of the subject to side effects. Some of the proteases are more potent than others. Preferred dosages for a given enzyme are readily determinable by those of skill in the art by a variety of means. A preferred means is to measure the physiological potency of a given compound.

The compositions of the invention can be used for prophylactic as well as therapeutic purposes. As used herein, the term "treating" refers both to the prevention of disease and the treatment of a disease or a pre-existing condition and more generally refers to the prevention of gluten ingestion from having a toxic effect on the patient or reducing the toxicity, relative to the toxic effect of ingestion of the same amount of gluten in the absence of protease therapy. The invention provides a significant advance in the treatment of ongoing disease, and helps to stabilize and/or improve the clinical symptoms of the patient. Such treatment is desirably performed prior to loss of function in the affected tissues but can also help to restore lost function or prevent further loss of function. Evidence of therapeutic effect may be any diminution in the severity of disease, particularly as measured by the severity of symptoms such as fatigue, chronic diarrhea, malabsorption of nutrients, weight loss, abdominal distension, anemia, skin rash, and other symptoms of celiac disease and/or dermatitis herpetiformis and/or gluten sensitivity. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, and the like.

Patients that may be treated by the methods of the invention include those diagnosed with celiac disease or other gluten intolerance through one or more of serological tests, e.g. anti-gliadin antibodies, anti-transglutaminase antibodies, anti-endomysial antibodies; endoscopic evaluation, e.g. to identify celiac lesions; histological assessment of small intestinal mucosa, e.g. to detect villous atrophy, crypt hyperplasia, infiltration of intra-epithelial lymphocytes; and any GI symptoms dependent on inclusion of gluten in the diet.

Given the safety of oral proteases, they also find a prophylactic use in high-risk populations, such as Type I diabetics, family members of diagnosed celiac disease patients, dermatitis herpetiformis patients, HLA-DQ2 positive individuals, and/or patients with gluten-associated symptoms that have not yet undergone formal diagnosis. Such patients may be treated with regular-dose or low-dose (10-50% of the regular dose) enzyme. Similarly, temporary high-dose use of such an agent is also anticipated for patients recovering from gluten-mediated enteropathy in whom gut function has not yet returned to normal, for example as judged by fecal fat excretion assays.

Patients that can benefit from the present invention may be of any age and include adults and children. Children in particular benefit from prophylactic treatment, as prevention of early exposure to toxic gluten peptides can prevent initial development of the disease. Children suitable for prophylaxis can be identified by genetic testing for predisposition, e.g. by HLA typing, by family history, by T cell assay, or by other medical means. As is known in the art, dosages may be adjusted for pediatric use.

The therapeutic effect can be measured in terms of clinical outcome or can be determined by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of a disease.

Various methods for administration may be employed, preferably using oral administration, for example with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

The various aspects and embodiments of the invention are illustrated without limitation in the following examples.

EXAMPLES

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

Favorable properties for proteases for degrading gluten in digestive setting include resistance to other proteases present in the digestive tract to enable longer endurance of enzymes; broad specificity towards peptide size to enable gluten degradation to smallest possible fragments and also to facilitate synergy in two proteases if a combination of enzymes is used; broad pH stability and operating range to enable enzymes to function under acidic gastric conditions; favorable kinetics to enable degradation of majority of gluten before gastric emptying; and a low $K_m$ for gluten to enable gluten degradation without significant retardation of gluten degradation rates at low gluten concentrations.

Enzymes have evolved with the above characteristics in several natural sources, including insects that derive proteins from dried grain products, e.g. flour beetles. Flour beetles include *Tribolium castaneum* (red flour beetle), *Tribolium confusum* (confused flour beetle); *Tribolium destructor* (destructive flour beetle); *Tenebrio molitor* (mealworm beetle); *Tenebrio obscurus*; and the like. A flour beetle gluten degrading enzyme has one or more of the following advantages: the part of the insect digestive system in which they act is acidic, therefore, functional pH range of the digestive enzymes is acidic; the enzymes are stable to oxidation; the enzymes are proteolytically stable, relative to other proteases, to other insect digestive proteases, because they have evolved to function in the presence of each other. Because many digestive proteases in insect are homologous to human digestive proteases, the proteolytic resistance property is transferable to human digestive setting. The digestive proteases have to break down proteins fast enough before the meal is excreted, so the enzymes have favorable kinetics for meal digestion. Many grains have gluten as a storage protein and therefore the digestive enzymes have evolved in an environment in which breakdown of gluten is advantageous to the insect. Because gluten is rich in glutamine and proline residues, these digestive enzyme proteases are efficient in cleaving gluten and other glutamine rich proteins.

*T. castaneum*'s genome was published (Nature, 452(7190): 949-55, 2008), and >200 putative proteases have been identified in the genome. Protease sequences have been catalogued and have been assigned a putative function based on comparison with proteases of known function. Similarly, for *T. molitor*, the larval midgut cDNA transcripts were analyzed and proteases expressed in the larval midgut were identified and catalogued (Insect Molecular Biology (2007) 16 (4), 455-468). In accordance with the invention, several of these proteases were selected as glutamine specific glutenases by homology to EP-B2 (endoprotease-isoform B from barley), a known cysteine protease that degrades gluten, or by similarity to cathepsin-L-(a cysteine protease similar to EP-B2)-like midgut specific proteases. These proteases are listed in Table 1, above, and in the sequence listing.

Cloning and expression of glutamine proteases in *Escherichia coli* (*E. coli*): Codon optimized nucleotide sequences (SEQ ID NO: 10-13) were synthesized and cloned into pET28b vector (Novagen) between NcoI and BamHI sites for the cytosolic expression in *E. coli* strain BL21 (DE3). The chemical competent cells were prepared and transformed with expression plasmid. The expression plasmids contained the kan+ gene to provide resistance to the antibiotic kanamycin. Transformation of the *E. coli* strains with the expression plasmids enabled the strain to grow on medium containing kanamycin. The transformants were selected on kanamycin containing plates and screened for expression of the proteases.

For protein expression, a 10 mL starter culture was grown for 12 hours in Luria Broth (LB) in a 50 mL Falcon tube at 37° C. with shaking at 250 rpm. The starter culture was used to inoculate 1000 mL of LB in a 2 L shake flask. Cells were grown at 37° C. with shaking at 250 rpm to an optical density (OD600) of 0.6-0.8 measured by absorbance at 600 nm. Cells were cooled below 30° C. and Isopropyl β-D-1-thiogalactopyranoside (IPTG) was added to a concentration of 0.2-1 mM to induce protein expression under the control of IPTG inducible T7 promoter. Protein was expressed for 12 hours at 30° C. with shaking at 250 rpm.

Proteases expressed well in this expression system as inclusion bodies (IB). The fermentation yield was approximately 5-100 mg/L of protease. XP_970838 expressed at ~100 mg/L levels.

Refolding and purification of glutamine specific cysteine proteases: Cells were harvested by centrifugation at 5000×g for 15 minutes. Harvested cells were resuspended in lysis buffer (50 mM Tris, pH 8.5, 2 mM MTG). The cells were lysed by sonication and inclusion bodies were separated from soluble matter by centrifugation at 10,000×g for 30 minutes. For washing, inclusion bodies were resuspended in water to ½ of the original volume. Inclusion bodies were recovered by centrifugation at 10,000×g for 30 minutes. The inclusion body washing process was repeated once. Washed inclusion bodies were solubilized in solubilization buffer (50 mM Tris, pH 8.5, 2 mM MTG, 7 M urea) for 4-6 hours at room temperature in ½ the original volume. After solubilization, insoluble matter was removed by centrifugation at 10,000×g for 30 minutes. Protein refolding was carried out by diluting protein 1 to 20 fold in 10 mM sodium phosphate, pH 8.2, 880 mM arginine, 1 mM GSH (reduced glutathione) and 1 mM GSSG (oxidized glutathione) at 4° C. and incubating overnight. After refolding, the protein mixture was concentrated and dialyzed against 50 mM Tris-HCl, pH 8.5 and 2 mM MTG at 4° C. for overnight for the removal of arginine. HisSelect Nickel affinity resin, pre-equilibrated in 50 mM Tris, 2 mM MTG (pH 8.5) was added to dialyzed protein. The suspension was shaken at 2-8° C. for 2 hours for batch binding of the protein to the resin. The slurry was packed into a Kontes gravity flow column. The resin bed was washed with 50 mM Tris, 2 mM MTG (pH 8.5). Protein was eluted in 100 mM Tris, 2 mM MTG and 200 mM imidazole (pH 8.5). Eluted protein was dialyzed against 100 mM Tris-HCl, pH 8.5, 5 mM EDTA, 2 mM MTG and 2.5% Mannitol at 4° C. for overnight. Dialyzed protein was further concentrated, aliquot and stored at −80° C. The concentration of the protein was determined to be approximately 5 mg/mL based on quantification of the main band by SDS-PAGE gel.

Pepsin stability of proteases under low pH conditions: 0.5 mg/mL pre-activated XP_970838 was incubated with 0.4 mg/mL pepsin and 1 mg/mL BSA at pH 3.0 at 37 C. 12.5 μL of XP_970838 were taken at various timepoints and added to a chromogenic substrate Z-Phe-Arg-pNA and the activity was monitored at 410 nm by the release of pNA chromophore from substrate by proteolytic action of XP_970838. The data is shown below and indicates that XP_970838 has a half life of approximately 10 min, demonstrating that XP_970838 has high stability to short term exposure to highly concentrated pepsin in low pH environment. The resistance to pepsin in low pH environment is valuable for sustained activity of these proteases in diverse gastric environment.

TABLE 2

Stability of XP_970838 against proteolysis by pepsin at pH 3.0

| Time (min) | XP_970838 Activity (%) |
|---|---|
| 0 | 100.0 |
| 5 | 72.0 |
| 10 | 48.4 |
| 15 | 34.2 |
| 20 | 21.1 |
| 30 | 9.9 |

Stability of proteases under oxidizing conditions: A banana, ~335 mL 40 mM HCl and one Amy's Gluten Free Korma meal were mixed and incubated at room temperature for 30 min. The solids were removed by centrifugation and the supernatant, which oxidatively inactivates certain proteases was used for the following experiments. Pre-activated 0.5 mg/mL of XP_970838 was incubated with 70% of oxidizing meal supernatant at pH 4.0 at 37 C. 12.5 µL of XP_970838 were taken at various timepoints and added to a chromogenic substrate Z-Phe-Arg-pNA and the activity was monitored at 410 nm by the release of pNA chromophore from substrate by proteolytic action of XP_970838. The data is shown below and indicates that XP_970838 has a half-life of greater than 30 min, demonstrating that XP_970838 has very high stability to exposure to oxidizing conditions. The resistance to oxidation is valuable for sustained activity of these proteases in diverse gastric environments.

TABLE 3

Stability of XP_970838 under oxidative conditions

| Time (min) | XP_970838 Activity (%) |
|---|---|
| 0 | 100 |
| 5 | 89.2 |
| 10 | 81.4 |
| 15 | 80.2 |
| 20 | 71.3 |
| 30 | 68.3 |
| 60 | 64.1 |

High pH stability of activated XP_970838: 0.5 mg/mL of pre-activated XP_970838 was incubated with 250 mM Tris at pH 7.5 at 37° C. 12.5 µL of XP_970838 were taken at various timepoints and added to a chromogenic substrate Z-Phe-Arg-pNA and the activity monitored at 410 nm by the release of pNA chromophore from substrate by proteolytic action of XP_970838. The data is shown below and indicates that XP_970838 has a half-life of greater than 30 min, demonstrating that XP_970838 has very high stability to exposure to high pH conditions. The resistance to high pH condition is valuable for sustained activity of these proteases in diverse gastric environments.

TABLE 4

Stability of XP_970838 at high pH condition

| Time (min) | XP_970838 Activity (%) |
|---|---|
| 0 | 100.0 |
| 3 | 99.9 |
| 5 | 96.1 |
| 10 | 93.3 |
| 30 | 88.3 |
| 60 | 85.7 |

Degradation of gluten: 30 mg of dried bread crumbs containing approximately 5 mg of gluten were incubated with 0.2 mg/mL of pre-activated XP_970838, 0.2 mg/mL of XP_972061 (see PCT Pub. No. 2011/126873, incorporated herein by reference) or the combination of the two proteases in 1 mL reaction at 37° C. for 30 minutes under the following conditions: 1) pH 3.0, 4.0 and 6.5 to evaluate the efficacy of individual enzymes in a wide range of post-prandial pHs, 2) pH 3.0 and 4.0 in the presence of 0.4 mg/mL porcine pepsin to evaluate the efficacy and stability of the two proteases in the presence of gastric peptidase, and 3) pH 4.0 in the presence of an oxidative meal supernatant to evaluate the efficacy and stability of XP_970838 in oxidative gastric conditions. The gluten degradation was analyzed quantitatively by ELISA (data tabulated below) which measures one of the immunostimulatory epitopes relevant to celiac disease. XP_970838 showed significant gluten degradation at pH 3.0, 4.0, and 6.5 demonstrating that the enzyme is stable and effective in a broad range of pH that may be encountered in gastric environment. XP_970838 showed significant gluten degradation in the presence of highly concentrated pepsin at pH 3.0 and 4.0, demonstrating that XP_970838 is resistant to proteolytic degradation by pepsin, commonly present in gastric environment. XP_970838 also showed significant gluten degradation in an oxidative meal supernatant, demonstrating that XP_970838 is less prone to inactivation in oxidative conditions which may be encountered in some common meals. Overall, XP_970838 showed robust gluten degradation in a wide range of conditions that may be encountered in the gastric compartment, demonstrating that the enzyme has optimal properties to function in a dynamic gastric environment. XP_972061 complemented XP_970838 at pH 3.0, 4.0, and 6.0 with or without pepsin, indicated by improved gluten degradation in a wide range of conditions. These results combined with stability results above show that XP_970838 can be used alone or in combination with XP_972061 in a mutually compatible formulation to obtain significant gluten degradation in stomach.

TABLE 5

Quantitative analysis of degradation of immunostimulatory epitope in whole wheat bread crumbs by XP_970838 and XP_972061

| XP_970838, mg/mL | XP_972061, mg/mL | pH | Oxidative meal, % | Porcine pepsin, mg/mL | Fold degradation of Gluten relative to no enzyme control |
|---|---|---|---|---|---|
| 0.2 | 0 | 3.0 | 0 | 0 | 7.3 |
| 0 | 0.2 | 3.0 | 0 | 0 | 1.0 |
| 0.2 | 0.2 | 3.0 | 0 | 0 | 11.7 |
| 0.2 | 0 | 4.0 | 0 | 0 | 13.9 |
| 0 | 0.2 | 4.0 | 0 | 0 | 1.0 |
| 0.2 | 0.2 | 4.0 | 0 | 0 | 20.8 |
| 0.2 | 0 | 6.5 | 0 | 0 | 5.4 |
| 0 | 0.2 | 6.5 | 0 | 0 | 0.6 |
| 0.2 | 0.2 | 6.5 | 0 | 0 | 7.2 |
| 0.2 | 0 | 3.0 | 0 | 0.4 | 7.0 |
| 0 | 0.2 | 3.0 | 0 | 0.4 | 1.0 |
| 0.2 | 0.2 | 3.0 | 0 | 0.4 | 5.1 |
| 0.2 | 0 | 4.0 | 0 | 0.4 | 5.2 |
| 0 | 0.2 | 4.0 | 0 | 0.4 | 1.2 |
| 0.2 | 0.2 | 4.0 | 0 | 0.4 | 14.9 |
| 0.2 | 0 | 4.0 | 70 | 0.4 | 12.9 |

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

The invention claimed is:

1. A method for treating gluten intolerance in a patient in need of such treatment, wherein said treatment reduces exposure of said patient to immunogenic gluten peptides, said method comprising:
orally administering to said patient a therapeutically effective dose of an isolated, purified or recombinant form of one or more proteases selected from an insect protease comprising a sequence set forth in any one of SEQ ID NO:1, 2, 3, 4, 10, 11, 12, or 13 contemporaneously with the ingestion of a food that may contain gluten.

2. The method of claim 1, further comprising orally administering to said patient a therapeutically effective dose of one or more non-insect proteases.

3. The method of claim 2, wherein said non-insect protease is one or more of Hordeum vulgare endoprotease (Genbank accession U19384); X-Pro dipeptidase from Aspergillus oryzae (GenBank ID# BD191984); carboxypeptidase from Aspergillus saitoi (GenBank ID# D25288); Flavobacterium meningosepticum PEP (Genbank ID # D10980); Sphingomonas capsulate PEP (GenBank ID# AB010298); Penicillium citrinum PEP (GenBank ID# D25535); Lactobacillus helveticus PEP (GenBank ID# 321529); and Myxococcus xanthus PEP (GenBank ID# AF127082).

4. The method of claim 1, wherein said upon ingestion with a gluten containing foodstuff said protease degrades the gluten to fragments shorter than 8 amino acids.

5. A method for treating gluten intolerance in a patient in need of such treatment, the method comprising:
orally administering to said patient a pharmaceutical formulation comprising an effective dose of an isolated, purified or recombinant form of an insect protease comprising the amino acid sequence set forth in SEQ ID NO:2 or SEQ ID NO:11 in a unit dose pharmaceutical formulation comprising a pharmaceutically acceptable excipient, contemporaneously with the ingestion of a food that may contain gluten.

6. The method of claim 5, further comprising orally administering to said patient a therapeutically effective dose of one or more non-insect proteases.

7. The method of claim 6, wherein said non-insect protease is one or more of Hordeum vulgare endoprotease (Genbank accession U19384); X-Pro dipeptidase from Aspergillus oryzae (GenBank ID# BD191984); carboxypeptidase from Aspergillus saitoi (GenBank ID# D25288); Flavobacterium meningosepticum PEP (Genbank ID # D10980); Sphingomonas capsulata PEP (GenBank ID# AB010298); Penicillium citrinum PEP (GenBank ID# D25535); Lactobacillus helveticus PEP (GenBank ID# 321529); and Myxococcus xanthus PEP (GenBank ID# AF127082).

8. A method for treating gluten intolerance in a patient in need of such treatment, the method comprising:
orally administering to said patient a pharmaceutical formulation comprising:
an isolated, purified or recombinant form of a protease comprising the amino acid sequence set forth in SEQ ID NO:2 or SEQ ID NO:11 in a unit dose of 0.01 mg to 500 mg /kg body weight, which upon oral administration by the patient is effective to cleave an ingested gluten oligopeptide to fragments shorter than 8 amino acids;
and a pharmaceutically acceptable excipient.

9. The method of claim 8, further comprising orally administering to said patient a therapeutically effective dose of one or more non-insect proteases.

10. The method of claim 9, wherein said non-insect protease is one or more of Hordeum vulgare endoprotease (Genbank accession U19384); X-Pro dipeptidase from Aspergillus oryzae (GenBank ID# BD191984); carboxypeptidase from Aspergillus saitoi (GenBank ID# D25288); Flavobacterium meningosepticum PEP (Genbank ID # D10980); Sphingomonas capsulate PEP (GenBank ID# AB010298); Penicillium citrinum PEP (GenBank ID# D25535); Lactobacillus helveticus PEP (GenBank ID# 321529); and Myxococcus xanthus PEP (GenBank ID# AF127082).

* * * * *

SEQUENCE LISTING

<160> NUMBER OF SEQ ID NOS: 13

<210> SEQ ID NO 1
<211> LENGTH: 322
<212> TYPE: PRT
<213> ORGANISM: Tribolium castaneum

<400> SEQUENCE: 1

Met Val Ser Phe Phe Asp Leu Val Gln Glu Gln Trp Gly Ala Phe Lys
1               5                   10                  15

Val Thr His Lys Lys Gln Tyr Glu Ser Glu Thr Glu Glu Arg Phe Arg
            20                  25                  30

Met Lys Ile Phe Met Glu Asn Ala His Lys Val Ala Lys His Asn Lys
        35                  40                  45

Leu Tyr Ala Gln Gly Leu Val Ser Phe Lys Leu Gly Val Asn Lys Tyr
    50                  55                  60

Ser Asp Met Leu Asn His Glu Phe Val His Thr Leu Asn Gly Tyr Asn
65                  70                  75                  80

Arg Ser Lys Thr Pro Leu Arg Ser Gly Glu Leu Asp Glu Ser Ile Thr
                85                  90                  95

Phe Ile Pro Pro Ala Asn Val Glu Leu Pro Lys Gln Ile Asp Trp Arg
            100                 105                 110

Lys Leu Gly Ala Val Thr Pro Val Lys Asp Gln Gly Gln Cys Gly Ser
        115                 120                 125

Cys Trp Ser Phe Ser Thr Thr Gly Ser Leu Glu Gly Gln His Phe Arg
    130                 135                 140

Lys Ser Lys Lys Leu Val Ser Leu Ser Glu Gln Asn Leu Ile Asp Cys
145                 150                 155                 160

Ser Glu Lys Tyr Gly Asn Asn Gly Cys Asn Gly Gly Leu Met Asp Asn
                165                 170                 175

Ala Phe Arg Tyr Ile Lys Asp Asn Gly Gly Ile Asp Thr Glu Gln Ser
            180                 185                 190

Tyr Pro Tyr Lys Ala Glu Asp Glu Lys Cys His Tyr Lys Pro Arg Asn
        195                 200                 205

Lys Gly Ala Thr Asp Arg Gly Phe Val Asp Ile Glu Ser Gly Asp Glu
    210                 215                 220

Glu Lys Leu Lys Ala Ala Val Ala Thr Val Gly Pro Ile Ser Val Ala
225                 230                 235                 240

Ile Asp Ala Ser His Pro Thr Phe Gln Gln Tyr Ser Glu Gly Val Tyr
                245                 250                 255

Tyr Glu Pro Glu Cys Ser Ser Glu Gln Leu Asp His Gly Val Leu Val
            260                 265                 270

Val Gly Tyr Gly Thr Asp Glu Asp Gly Asn Asp Tyr Trp Leu Val Lys
        275                 280                 285

Asn Ser Trp Gly Asp Ser Trp Gly Asp Gln Gly Tyr Ile Lys Met Ala
    290                 295                 300

Arg Asn Arg Asp Asn Asn Cys Gly Ile Ala Thr Gln Ala Ser Tyr Pro
305                 310                 315                 320

Leu Val

<210> SEQ ID NO 2
<211> LENGTH: 310
<212> TYPE: PRT
<213> ORGANISM: Tribolium castaneum

<400> SEQUENCE: 2

Met Ser Pro Val His Ala Lys Trp Ala Glu Phe Lys Leu Thr His Lys
1               5                   10                  15

Lys Gln Tyr Ser Ser Pro Ile Glu Glu Leu Arg Arg Lys Ala Ile Phe
            20                  25                  30

Gln Asp Asn Leu Val Lys Ile Glu Glu His Asn Ala Lys Phe Ala Lys
            35                  40                  45

Gly Glu Val Thr Tyr Thr Lys Ala Val Asn Gln Phe Ala Asp Met Thr
50                  55                  60

Ala Asp Glu Phe Met Ala Tyr Val Asn Arg Gly Leu Ala Thr Lys Pro
65                  70                  75                  80

Lys Met Asn Glu Lys Leu Arg Ile Pro Phe Val Lys Ser Gly Lys Pro
                85                  90                  95

Ala Ala Ala Glu Val Asp Trp Arg Ser Lys Ala Val Thr Glu Val Lys
                100                 105                 110

Asp Gln Gly Gln Cys Gly Ser Cys Trp Ser Phe Ser Thr Thr Gly Ala
            115                 120                 125

Val Glu Gly Gln Leu Ala Ile Ser Gly Lys Gly Leu Thr Ser Leu Ser
130                 135                 140

Glu Gln Asn Leu Val Asp Cys Ser Ser Gln Tyr Gly Asn Ala Gly Cys
145                 150                 155                 160

Asn Gly Gly Trp Met Asp Ser Ala Phe Asp Tyr Ile His Asp Asn Gly
                165                 170                 175

Ile Met Ser Glu Ser Ala Tyr Pro Tyr Thr Ala Met Asp Gly Asn Cys
                180                 185                 190

Arg Phe Asp Ala Ser Gln Ser Val Thr Ser Leu Gln Gly Tyr Tyr Asp
            195                 200                 205

Ile Pro Ser Gly Asp Glu Ser Ala Leu Gln Asp Ala Val Ala Asn Asn
210                 215                 220

Gly Pro Val Ala Val Ala Leu Asp Ala Thr Glu Glu Leu Gln Leu Tyr
225                 230                 235                 240

Ser Gly Gly Val Leu Tyr Asp Thr Thr Cys Ser Ala Gln Ala Leu Asn
                245                 250                 255

His Gly Val Leu Val Val Gly Tyr Gly Ser Glu Gly Gly Gln Asp Tyr
                260                 265                 270

Trp Ile Val Lys Asn Ser Trp Gly Ser Gly Trp Gly Glu Gln Gly Tyr
            275                 280                 285

Trp Arg Gln Ala Arg Asn Arg Asn Asn Cys Gly Ile Ala Thr Ala
290                 295                 300

Ala Ser Tyr Pro Ala Leu
305                 310

<210> SEQ ID NO 3
<211> LENGTH: 314
<212> TYPE: PRT
<213> ORGANISM: Tribolium castaneum

<400> SEQUENCE: 3

Met Ala Ser Pro Gln Lys Leu Ile Asn Asp Gln Asn Trp Ser Gln Phe
1               5                   10                  15

Lys Leu Thr His Lys Lys Glu Tyr Ser Thr Lys Thr Glu Glu Met Lys
            20                  25                  30

Arg Leu Ala Ile Phe Thr Glu Asn Leu Ser Lys Ile Asp Ala His Asn
            35                  40                  45

Thr Lys Tyr Arg Asn Gly Glu Val Thr Tyr Phe Lys Ala Met Asn Lys

```
            50                  55                  60
Phe Gly Asp Leu Thr Thr Asp Glu Phe Leu Ala Phe Val Asn Arg Asn
 65                  70                  75                  80

Lys Leu Thr Lys Arg Glu Lys Asn Glu Lys His Thr Lys Leu Asn Thr
                 85                  90                  95

Thr Lys Ile Glu Tyr Glu Thr Gln Val Asp Trp Arg Ala Asn Gly Leu
                100                 105                 110

Val Ser Asp Val Lys Asn Glu Gln Asp Cys Ser Ser Ser Trp Ser Phe
                115                 120                 125

Ser Ala Leu Gly Ala Val Glu Gly Gln Leu Ala Leu Lys Thr Asn Gln
                130                 135                 140

Leu Thr Ser Leu Ser Ala Gln Asn Leu Ile Asp Cys Ser Ala Asp Phe
145                 150                 155                 160

Gly Cys Asn Gly Gly His Ala Thr Asn Ala Tyr Ser Tyr Ile Ser Gln
                165                 170                 175

Phe Gly Ile Met Pro Glu Lys Asp Tyr Pro Tyr Glu Gly Lys Ala Gly
                180                 185                 190

Val Cys Arg Phe Asp Ala Ser Lys Ser Ile Thr Thr Val Thr Gly Phe
                195                 200                 205

Tyr Asp Ile Asp Pro Asn Asp Glu Thr Ala Leu Gln Gly Ala Leu Ala
                210                 215                 220

Met Met Gly Pro Ile Ala Ala Thr Ile Glu Ala Thr Glu Glu Leu Gln
225                 230                 235                 240

Phe Tyr Lys Gly Gly Ile Leu Leu Asp Glu Lys Cys Asn Ser Lys Val
                245                 250                 255

Pro Asp Leu Asn His Gly Val Leu Val Val Gly Tyr Gly Ser Glu Asn
                260                 265                 270

Gly Gly Asp Phe Trp Ile Val Lys Asn Ser Trp Gly Ser Asp Trp Gly
                275                 280                 285

Glu Gly Gly Tyr Tyr Arg Pro Val Arg Asn His Gly Asn Asn Cys Gly
                290                 295                 300

Ile Ala Ser Ser Ala Thr Leu Pro Ile Leu
305                 310

<210> SEQ ID NO 4
<211> LENGTH: 313
<212> TYPE: PRT
<213> ORGANISM: Tenebrio molitor

<400> SEQUENCE: 4

Met Leu Pro Lys Ser Pro Phe Gln Glu Gln Trp Ser Gln Phe Lys Leu
  1               5                  10                  15

Thr His Lys Lys Ser Tyr Ser Ser Pro Ile Glu Glu Ile Arg Arg Gln
                 20                  25                  30

Leu Ile Phe Lys Asp Asn Val Ala Lys Ile Ala Glu His Asn Ala Lys
                 35                  40                  45

Phe Glu Lys Gly Glu Val Thr Tyr Ser Lys Ala Met Asn Gln Phe Gly
                 50                  55                  60

Asp Met Ser Lys Glu Glu Phe Leu Ala Tyr Val Asn Arg Gly Lys Ala
 65                  70                  75                  80

Gln Lys Pro Lys His Pro Glu Asn Leu Arg Met Pro Tyr Val Phe Ser
                 85                  90                  95

Lys Lys Pro Leu Ala Ala Ser Val Asp Trp Arg Ser Asn Ala Val Ser
                100                 105                 110
```

```
Glu Val Lys Asp Gln Gly Gln Cys Gly Ser Cys Trp Ser Phe Ser Thr
        115                 120                 125

Thr Gly Ala Val Glu Gly Gln Leu Ala Leu Gln Arg Gly Gly Leu Thr
    130                 135                 140

Ser Leu Ser Glu Gln Asn Leu Ile Asp Cys Ser Ser Ser Tyr Gly Asn
145                 150                 155                 160

Ala Gly Cys Asp Gly Gly Trp Met Asp Ser Ala Phe Ser Tyr Ile His
                165                 170                 175

Asp Tyr Gly Ile Met Ser Glu Ser Tyr Pro Tyr Glu Ala Gln Asp
            180                 185                 190

Asp Tyr Cys Arg Phe Asp Ser Ser Gln Ser Val Thr Thr Leu Ser Gly
        195                 200                 205

Tyr Tyr Asp Leu Pro Ser Gly Asp Glu Asn Ser Leu Ala Asp Ala Val
    210                 215                 220

Gly Gln Ala Gly Pro Val Ala Val Ala Ile Asp Ala Thr Asp Glu Leu
225                 230                 235                 240

Gln Phe Tyr Ser Gly Gly Leu Phe Tyr Asp Gln Thr Cys Asn Gln Ser
                245                 250                 255

Asp Leu Asn His Gly Val Phe Val Val Gly Tyr Gly Ser Asp Asn Gly
            260                 265                 270

Gln Asp Tyr Trp Ile Leu Lys Asn Ser Trp Gly Ser Gly Trp Gly Glu
        275                 280                 285

Asn Gly Tyr Trp Thr Gln Val Arg Asn Tyr Gly Asn Asn Cys Gly Ile
    290                 295                 300

Ala Thr Ala Ala Ser Tyr Pro Ala Leu
305                 310

<210> SEQ ID NO 5
<211> LENGTH: 339
<212> TYPE: PRT
<213> ORGANISM: Dermestes frischii
<220> FEATURE:
<221> NAME/KEY: VARIANT
<222> LOCATION: 61, 136
<223> OTHER INFORMATION: Xaa = Any Amino Acid

<400> SEQUENCE: 5

Met Lys Phe Phe Val Leu Ala Leu Val Phe Ile Val Gly Ala Gln Ala
1               5                   10                  15

Val Ser Phe Phe Asp Leu Val Gln Glu Gln Trp Gly Thr Phe Lys Leu
                20                  25                  30

Gln His Lys Lys Gln Tyr Lys Ser Asp Thr Glu Glu Lys Phe Arg Met
            35                  40                  45

Lys Ile Phe Met Glu Asn Ser His Lys Val Ala Lys Xaa Asn Lys Leu
        50                  55                  60

Tyr Glu Met Gly Leu Val Ser Tyr Lys Leu Lys Ile Asn Lys Tyr Ala
65                  70                  75                  80

Asp Met Leu His His Glu Phe Val His Thr Val Asn Gly Phe Asn Arg
                85                  90                  95

Thr Lys Asn Thr Pro Leu Leu Gly Thr Ser Glu Asp Glu Gln Gly Ala
            100                 105                 110

Thr Phe Ile Ala Pro Ala Asn Val Lys Phe Pro Glu Asn Val Asp Trp
        115                 120                 125

Arg Glu His Gly Ala Val Thr Xaa Val Lys Asp Gln Gly His Cys Gly
    130                 135                 140

Ser Cys Trp Ser Phe Ser Ala Thr Gly Ala Leu Glu Gly Gln His Phe
```

```
145                 150                 155                 160
Arg Lys Thr Asn Lys Leu Val Ser Leu Ser Glu Gln Asn Leu Val Asp
                165                 170                 175

Cys Ser Thr Lys Phe Gly Asn Asp Gly Cys Asn Gly Gly Leu Met Asp
                180                 185                 190

Asn Ala Phe Lys Tyr Val Lys Tyr Asn His Gly Ile Asp Thr Glu Ala
                195                 200                 205

Ser Tyr Pro Tyr His Ala Asp Asp Glu Lys Cys His Tyr Asn Pro Lys
        210                 215                 220

Thr Ser Gly Ala Thr Asp Arg Gly Phe Val Asp Ile Pro Thr Gly Asp
225                 230                 235                 240

Glu Glu Lys Leu Met Ala Ala Val Ala Thr Val Gly Pro Val Ser Val
                245                 250                 255

Ala Ile Asp Ala Ser His Glu Ser Phe Gln Leu Tyr Ser Glu Gly Val
                260                 265                 270

Tyr Tyr Asp Pro Glu Cys Ser Ser Glu Glu Leu Asp His Gly Val Leu
                275                 280                 285

Val Val Gly Tyr Gly Thr Asp Glu Asn Gly Gln Asp Tyr Trp Ile Val
        290                 295                 300

Lys Asn Ser Trp Gly Glu Ser Trp Gly Glu Gln Gly Tyr Ile Lys Met
305                 310                 315                 320

Ala Arg Asn Arg Asp Asn Asn Cys Gly Ile Ala Thr Gln Ala Ser Tyr
                325                 330                 335

Pro Leu Val

<210> SEQ ID NO 6
<211> LENGTH: 323
<212> TYPE: PRT
<213> ORGANISM: Myxine glutinosa

<400> SEQUENCE: 6

Met Thr Arg Val Phe Val Leu Leu Ala Leu Val Val Ala Ala Asn Ala
  1               5                  10                  15

Leu Asp Trp Glu Ser Trp Lys Gly Lys Tyr Gly Lys Ser Tyr Leu Gly
                 20                  25                  30

Arg Gly Glu Glu Val Leu Arg Lys Arg Val Trp Glu Ser Asn Leu Gln
             35                  40                  45

Ile Val Gln Gln His Asn Val Leu Ala Asp Gln Gly Gln Ala Asn Tyr
         50                  55                  60

Arg Leu Gly Met Asn Thr Tyr Ala Asp Leu Tyr Asn Glu Glu Phe Met
65                  70                  75                  80

Ala Leu Lys Gly Ser Gly Gly Leu Leu Gln Ala Lys Asp Lys Ser Ser
                 85                  90                  95

Thr Gln Thr Phe Lys Pro Leu Val Gly Val Thr Leu Pro Ser Ser Val
                100                 105                 110

Asp Trp Arg Asn Gln Gly Tyr Val Thr Pro Val Lys Asp Gln Gly Gln
            115                 120                 125

Cys Gly Ser Cys Trp Thr Phe Ser Ala Thr Gly Ser Leu Glu Gly Gln
        130                 135                 140

His Phe Ala Lys Thr Gly Asn Leu Leu Ser Leu Ser Glu Gln Gln Leu
145                 150                 155                 160

Val Asp Cys Ala Gly Arg Tyr Gly Asn Tyr Gly Cys Asn Gly Gly Leu
                165                 170                 175

Met Glu Ser Ala Tyr Asp Tyr Ile Lys Gly Val Gly Gly Val Glu Leu
```

```
            180                 185                 190
Glu Ser Ala Tyr Pro Tyr Thr Ala Arg Asp Gly Arg Cys Lys Phe Asp
        195                 200                 205

Arg Ser Lys Val Val Ala Thr Cys Lys Gly Tyr Val Val Ile Pro Val
    210                 215                 220

Gly Asp Glu Gln Ala Leu Met Gln Ala Val Gly Thr Ile Gly Pro Val
225                 230                 235                 240

Ala Val Ser Ile Asp Ala Ser Gly Tyr Ser Phe Gln Leu Tyr Glu Ser
                245                 250                 255

Gly Val Tyr Asp Phe Arg Arg Cys Ser Ser Thr Asn Leu Asp His Gly
                260                 265                 270

Val Leu Ala Val Gly Tyr Gly Thr Glu Gly Gly Gln Asn Tyr Trp Leu
            275                 280                 285

Val Lys Asn Ser Trp Gly Pro Gly Trp Gly Asp Gln Gly Tyr Ile Lys
            290                 295                 300

Met Ser Lys Asp Lys Asn Asn Gln Cys Gly Ile Ala Thr Asp Ser Cys
305                 310                 315                 320

Tyr Pro Leu

<210> SEQ ID NO 7
<211> LENGTH: 316
<212> TYPE: PRT
<213> ORGANISM: Rhodnius prolixus

<400> SEQUENCE: 7

Met Leu Ile Pro Ser Phe Asp Ile Asp Pro Gln Glu Trp Leu Ala Phe
1               5                   10                  15

Lys Ala Met His Gly Lys Asn Tyr Arg Asn Gln Phe Glu Glu Ile Phe
            20                  25                  30

Arg Met Lys Val Phe Ile Asp Asn Lys Lys Ile Asp Glu His Asn
        35                  40                  45

Ala Lys Tyr Glu Leu Gly Glu Ala Ser Tyr Lys Met Lys Met Asn His
    50                  55                  60

Leu Gly Asp Leu Met Val His Glu Phe Lys Ala Leu Met Asn Gly Phe
65                  70                  75                  80

Lys Lys Thr Pro Asn Ala Glu Arg Asn Gly Lys Ile Tyr Val Pro Ser
                85                  90                  95

Asn Glu Asn Leu Pro Lys Ser Val Asp Trp Arg Gln Arg Gly Ala Val
            100                 105                 110

Thr Pro Val Lys Asp Gln Gly His Cys Gly Ser Cys Trp Ser Phe Ser
        115                 120                 125

Ala Thr Gly Ser Leu Glu Gly Gln Leu Phe Leu Lys Thr Gly Arg Leu
    130                 135                 140

Val Ser Leu Ser Glu Gln Asn Leu Val Asp Cys Ser Lys Thr Tyr Gly
145                 150                 155                 160

Asn Ser Gly Cys Glu Gly Gly Leu Met Asn Gln Ala Phe Gln Tyr Val
                165                 170                 175

Arg Asp Asn Lys Gly Ile Asp Thr Glu Ala Ser Tyr Pro Tyr Glu Ala
            180                 185                 190

Arg Glu Asn Asn Cys Arg Phe Lys Glu Asp Lys Val Gly Gly Thr Asp
        195                 200                 205

Lys Gly Tyr Val Asp Ile Leu Glu Ala Ser Glu Lys Asp Leu Gln Ser
    210                 215                 220

Ala Val Ala Thr Val Gly Pro Ile Ser Val Arg Ile Asp Ala Ser His
```

```
                225                 230                 235                 240
        Glu Ser Phe Gln Phe Tyr Ser Glu Gly Val Tyr Lys Glu Gln Tyr Cys
                        245                 250                 255

Ser Pro Ser Gln Leu Asp His Gly Val Leu Thr Val Gly Tyr Gly Thr
                        260                 265                 270

Glu Asn Gly Gln Asp Tyr Trp Leu Val Lys Asn Ser Trp Gly Pro Ser
                        275                 280                 285

Trp Gly Glu Ser Gly Tyr Ile Lys Ile Ala Arg Asn His Lys Asn His
                290                 295                 300

Cys Gly Ile Ala Ser Met Ala Ser Tyr Pro Val Val
        305                 310                 315

<210> SEQ ID NO 8
<211> LENGTH: 333
<212> TYPE: PRT
<213> ORGANISM: Hordeum vulgare

<400> SEQUENCE: 8

Met His Ala Ile Ser Val Leu Ala Val Leu Ala Leu Ala Phe Ser Cys
 1               5                  10                  15

Thr Leu Ala Phe Asp Ala Lys Leu Asn Gln His Trp Lys Leu Trp Lys
            20                  25                  30

Glu Ala Asn Asn Lys Arg Tyr Ser Asp Ala Glu Glu His Val Arg Arg
        35                  40                  45

Ala Thr Trp Glu Gly Asn Leu Gln Lys Val Gln Glu His Asn Leu Gln
    50                  55                  60

Ala Asp Leu Gly Val His Thr Tyr Trp Leu Gly Met Asn Lys Tyr Ala
65                  70                  75                  80

Asp Met Thr Val Thr Glu Phe Val Lys Val Met Asn Gly Tyr Asn Ala
                85                  90                  95

Thr Met Arg Gly Gln Arg Thr Gln Asp Arg His Thr Phe Ser Phe Asn
            100                 105                 110

Ser Lys Ile Ala Leu Pro Asp Thr Val Asp Trp Arg Asp Lys Gly Tyr
        115                 120                 125

Val Thr Asp Val Lys Asp Gln Gly Gln Cys Gly Ser Cys Trp Ala Phe
    130                 135                 140

Ser Thr Thr Gly Ala Leu Glu Gly Gln His Phe Lys Gln Thr Gly Lys
145                 150                 155                 160

Leu Val Ser Leu Ser Glu Gln Asn Leu Val Asp Cys Ser Gly Lys Gln
                165                 170                 175

Gly Asn Met Gly Cys Asn Gly Gly Leu Met Asp Gln Ala Phe Glu Tyr
            180                 185                 190

Ile Lys Glu Asn Asn Gly Ile Asp Thr Glu Asp Ser Tyr Pro Tyr Glu
        195                 200                 205

Ala Val Asp Asn Gln Cys Arg Phe Lys Ala Ala Asn Val Gly Ala Thr
    210                 215                 220

Asp Thr Gly Phe Thr Asp Ile Thr Ser Lys Asp Glu Ser Ala Leu Gln
225                 230                 235                 240

Gln Ala Val Ala Thr Val Gly Pro Ile Ser Val Ala Ile Asp Ala Gly
                245                 250                 255

His Thr Ser Phe Gln Leu Tyr Lys His Gly Val Tyr Asn Glu Pro Phe
            260                 265                 270

Cys Ser Gln Thr Arg Leu Asp His Gly Val Leu Ala Val Gly Tyr Gly
        275                 280                 285
```

```
Thr Asp Ser Gly Lys Asp Tyr Trp Leu Val Lys Asn Ser Trp Gly Glu
    290                 295                 300
Gly Trp Gly Asp Lys Gly Tyr Ile Lys Met Thr Arg Asn Lys Arg Asn
305                 310                 315                 320
Gln Cys Gly Ile Ala Thr Ala Ala Ser Tyr Pro Leu Val
                325                 330
```

<210> SEQ ID NO 9
<211> LENGTH: 321
<212> TYPE: PRT
<213> ORGANISM: Homarus americanus

<400> SEQUENCE: 9

```
Met Lys Val Val Ala Leu Phe Leu Phe Gly Leu Ala Leu Ala Ala Ala
  1               5                  10                  15
Asn Pro Ser Trp Glu Glu Phe Lys Gly Lys Phe Gly Arg Lys Tyr Val
                20                  25                  30
Asp Leu Glu Glu Glu Arg Tyr Arg Leu Asn Val Phe Leu Asp Asn Leu
            35                  40                  45
Gln Tyr Ile Glu Glu Phe Asn Lys Lys Tyr Glu Arg Gly Glu Val Thr
 50                  55                  60
Tyr Asn Leu Ala Ile Asn Gln Phe Ser Asp Met Thr Asn Glu Lys Phe
 65                  70                  75                  80
Asn Ala Val Met Lys Gly Tyr Lys Lys Gly Pro Arg Pro Ala Ala Val
                85                  90                  95
Phe Thr Ser Thr Asp Ala Ala Pro Glu Ser Thr Glu Val Asp Trp Arg
            100                 105                 110
Thr Lys Gly Ala Val Thr Pro Val Lys Asp Gln Gly Gln Cys Gly Ser
            115                 120                 125
Cys Trp Ala Phe Ser Thr Thr Gly Gly Ile Glu Gly Gln His Phe Leu
            130                 135                 140
Lys Thr Gly Arg Leu Val Ser Leu Ser Glu Gln Gln Leu Val Asp Cys
145                 150                 155                 160
Ala Gly Gly Ser Tyr Tyr Asn Gln Gly Cys Asn Gly Gly Trp Val Glu
                165                 170                 175
Arg Ala Ile Met Tyr Val Arg Asp Asn Gly Gly Val Asp Thr Glu Ser
            180                 185                 190
Ser Tyr Pro Tyr Glu Ala Arg Asp Asn Thr Cys Arg Phe Asn Ser Asn
            195                 200                 205
Thr Ile Gly Ala Thr Cys Thr Gly Tyr Val Gly Ile Ala Gln Gly Ser
            210                 215                 220
Glu Ser Ala Leu Lys Thr Ala Thr Arg Asp Ile Gly Pro Ile Ser Val
225                 230                 235                 240
Ala Ile Asp Ala Ser His Arg Ser Phe Gln Ser Tyr Tyr Thr Gly Val
                245                 250                 255
Tyr Tyr Glu Pro Ser Cys Ser Ser Ser Gln Leu Asp His Ala Val Leu
            260                 265                 270
Ala Val Gly Tyr Gly Ser Glu Gly Gly Gln Asp Phe Trp Leu Val Lys
            275                 280                 285
Asn Ser Trp Ala Thr Ser Trp Gly Glu Ser Gly Tyr Ile Lys Met Ala
            290                 295                 300
Arg Asn Arg Asn Asn Asn Cys Gly Ile Ala Thr Asp Ala Cys Tyr Pro
305                 310                 315                 320
Thr
```

<210> SEQ ID NO 10
<211> LENGTH: 1016
<212> TYPE: DNA
<213> ORGANISM: Tribolium castaneum

<400> SEQUENCE: 10

| | | |
|---|---|---|
| ccatgggcgt tctttctttt gatctggtgc aggaacaatg gggtgctttt aaagttaccc | 60 |
| ataagaaaca gtatgaatcc gaaactgaag aaagattccg catgaagatt tttatggaaa | 120 |
| acgcccacaa agtggcaaag cataataaac tgtacgcgca aggtctggtc tcattcaagc | 180 |
| tgggcgttaa caaatattcc gatatgctga atcacgaatt tgtgcatacc ctgaacggtt | 240 |
| acaatcgtag taagacccg ctgcgttctg gtgaactgga tgaatccatt accttcattc | 300 |
| ctccagctaa cgtggaactg ccgaaacaga ttgattggcg caagctgggc gccgttactc | 360 |
| ctgtgaaaga tcaaggacag tgtggctcat gctggtcctt tccaccacc ggatctttgg | 420 |
| aaggtcaaca cttccgtaag tccaaaaagc tggtctcatt gtccgaacag aatctgattg | 480 |
| attgttccga aaatatggt aacaatggct gcaacggtgg tctgatggat aatgcattta | 540 |
| gatacattaa ggataacggc ggtattgata ccgaacaatc ttatccatac aaagcggaag | 600 |
| atgaaaagtg tcattataaa ccgcgcaata agggcgctac tgatcgtggc ttcgttgaca | 660 |
| ttgaatccgg tgatgaagaa aaactgaaag ccgcagtggc gaccgtgggt cctatttcag | 720 |
| ttgctattga tgcctcccac ccaacctttc agcaatactc cgagggagtg tattacgaac | 780 |
| cggaatgctc ttccgaacag ctggatcatg gtgtcctggt tgtgggttat ggaaccgatg | 840 |
| aagatggtaa cgattactgg ctggttaaaa atagctgggg tgattcttgg ggtgatcaag | 900 |
| gttatattaa aatggcaaga aaccgtgata taactgtgg tattgctact caggcctcat | 960 |
| accctctggt gctggttcca cgtggaagtc atcaccatca ccatcactaa ggatcc | 1016 |

<210> SEQ ID NO 11
<211> LENGTH: 980
<212> TYPE: DNA
<213> ORGANISM: Tribolium castaneum

<400> SEQUENCE: 11

| | | |
|---|---|---|
| ccatgggctc tccggtgcat gctaaatggg ccgaatttaa gttgacccac aaaaagcagt | 60 |
| attcctcacc tattgaagaa ctgagacgca aagcaatttt ccaagataac ctggtgaaga | 120 |
| ttgaagaaca taatgcgaaa tttgctaagg gtgaggttac ttacaccaaa gccgtgaacc | 180 |
| agttcgcaga tatgaccgcg gatgaattta tggcttatgt caatcgtggt ctggccacca | 240 |
| agccaaaaat gaacgaaaag ttgagaatcc cgttcgttaa atccggcaag cctgcagcgg | 300 |
| ctgaagtgga ctggcgcagt aaagccgtga ctgaagttaa ggatcaagga cagtgtggct | 360 |
| cttgctggtc cttttcaacc accggcgcag tggaaggtca actggcgatt tccggtaaag | 420 |
| gcctgaccag tctgtctgaa cagaatctgg ttgattgttc ctcacaatac ggtaacgctg | 480 |
| gttgcaatgg cggttggatg gattccgcct tcgattatat tcacgataac ggtattatgt | 540 |
| ccgaatctgc ataccatat actgcgatgg acggcaattg tcgttttgat gcttcccagt | 600 |
| cagttacaag cctgcaagt tactatgata ttccgtccgg tgatgaatct gccctgcagg | 660 |
| atgcagtggc gaacaatggc cctgtggctg ttgccctgga tgcaaccgaa gaactgcaac | 720 |
| tgtactccgg tggtgtgctg tatgatacca cttgctcagc gcaggctctg aaccacggtg | 780 |
| tcctggtttgt gggttacggc agcgaaggtg gacaagatta ttggattgtt aaaaattcct | 840 |
| ggggttctgg ttgggggtgaa cagggttact ggagacaagc ccgcaaccgt aataacaatt | 900 |

| | |
|---|---|
| gtggtattgc aaccgccgct tcttatccag ctctgctggt tccacgtgga agtcatcacc | 960 |
| atcaccatca ctaaggatcc | 980 |

<210> SEQ ID NO 12
<211> LENGTH: 992
<212> TYPE: DNA
<213> ORGANISM: Tribolium castaneum

<400> SEQUENCE: 12

| | |
|---|---|
| ccatgggcgc ttctccgcag aaattgatta acgatcaaaa ttggtcccag tttaagctga | 60 |
| cccataaaaa ggaatattca actaaaaccg aagaaatgaa gagactggcc attttcaccg | 120 |
| aaaacctgtc caaaattgat gcacacaata ccaagtaccg caacggtgaa gtgacttatt | 180 |
| ttaaagcgat gaataagttc ggcgatttga ccaccgatga gtttctggct ttcgtgaacc | 240 |
| gtaataaatt gaccaagaga gaaagaacg aaaagcatac taaactgaat accaccaaga | 300 |
| ttgaatacga aacccaagtt gattggcgcg ccaacggcct ggtgtccgat gtgaaaaatg | 360 |
| aacaggattg ttcttcctca tggtcctttt ccgcactggg tgcggttgaa ggtcaactgg | 420 |
| ctctgaagac taaccagctg acatctctgt ccgcccaaaa tctgattgat tgctcagcag | 480 |
| atttcggctg taacggtggt cacgcgacca atgcttattc ctacatttcc cagtttggca | 540 |
| ttatgcctga aaagattat ccatacgagg gaaaggccgg tgtgtgccgt ttcgatgcat | 600 |
| ctaaatccat taccactgtg accggctttt atgatattga tccgaacgat gaaactgcgc | 660 |
| tgcaaggtgc tctggccatg atgggtccta ttgcagcgac cattgaagca accgaagaac | 720 |
| tgcagttcta caagggaggt atcttgctgg atgaaaaatg taattcaaaa gttccagact | 780 |
| tgaaccacgg tgtgctggtc gttggctatg gtagcgaaaa tggtggcgat ttttggattg | 840 |
| tgaaaaactc ttggggttcc gattggggtg aaggtggcta ctatagaccg gttcgtaatc | 900 |
| acggtaacaa ttgcggtatt gcctcatctg ctactctgcc tattctgctg gttccacgtg | 960 |
| gaagtcatca ccatcaccat cactaaggat cc | 992 |

<210> SEQ ID NO 13
<211> LENGTH: 992
<212> TYPE: DNA
<213> ORGANISM: Tenebrio molitor

<400> SEQUENCE: 13

| | |
|---|---|
| ccatgggcgc ttctccgcag aaattgatta acgatcaaaa ttggtcccag tttaagctga | 60 |
| cccataaaaa ggaatattca actaaaaccg aagaaatgaa gagactggcc attttcaccg | 120 |
| aaaacctgtc caaaattgat gcacacaata ccaagtaccg caacggtgaa gtgacttatt | 180 |
| ttaaagcgat gaataagttc ggcgatttga ccaccgatga gtttctggct ttcgtgaacc | 240 |
| gtaataaatt gaccaagaga gaaagaacg aaaagcatac taaactgaat accaccaaga | 300 |
| ttgaatacga aacccaagtt gattggcgcg ccaacggcct ggtgtccgat gtgaaaaatg | 360 |
| aacaggattg ttcttcctca tggtcctttt ccgcactggg tgcggttgaa ggtcaactgg | 420 |
| ctctgaagac taaccagctg acatctctgt ccgcccaaaa tctgattgat tgctcagcag | 480 |
| atttcggctg taacggtggt cacgcgacca atgcttattc ctacatttcc cagtttggca | 540 |
| ttatgcctga aaagattat ccatacgagg gaaaggccgg tgtgtgccgt ttcgatgcat | 600 |
| ctaaatccat taccactgtg accggctttt atgatattga tccgaacgat gaaactgcgc | 660 |
| tgcaaggtgc tctggccatg atgggtccta ttgcagcgac cattgaagca accgaagaac | 720 |

-continued

```
tgcagttcta caagggaggt atcttgctgg atgaaaaatg taattcaaaa gttccagact    780
tgaaccacgg tgtgctggtc gttggctatg gtagcgaaaa tggtggcgat ttttggattg    840
tgaaaaactc ttggggttcc gattggggtg aaggtggcta ctatagaccg gttcgtaatc    900
acggtaacaa ttgcggtatt gcctcatctg ctactctgcc tattctgctg gttccacgtg    960
gaagtcatca ccatcaccat cactaaggat cc                                  992
```